United States Patent
Zwart et al.

(10) Patent No.: US 6,371,910 B1
(45) Date of Patent: *Apr. 16, 2002

(54) INFLATABLE MANIPULATOR FOR ORGAN POSITIONING DURING SURGERY

(75) Inventors: Hans J. Zwart; Lawrence R. Tyler, both of Kettering, OH (US); Thomas J. Palermo, San Jose, CA (US); Kevin Van Bladel, San Mateo, CA (US); Roderick A. Young, Palo Alto, CA (US); James E. Jervis, Atherton, CA (US)

(73) Assignee: General Surgical Innovations, Inc., Norwalk, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/438,811

(22) Filed: Nov. 10, 1999

Related U.S. Application Data

(63) Continuation of application No. 08/951,799, filed on Oct. 16, 1997, now Pat. No. 6,015,382.

(51) Int. Cl.⁷ ................................................ A61B 1/32
(52) U.S. Cl. ................................................ 600/207
(58) Field of Search ................................. 600/201, 207, 600/235, 37, 206

(56) References Cited

U.S. PATENT DOCUMENTS

| | | | |
|---|---|---|---|
| 1,213,005 A | * 1/1917 | Pillsbury | |
| 4,263,900 A | * 4/1981 | Nicholson | 600/207 X |
| 5,183,464 A | * 2/1993 | Dubrul et al. | |
| 5,318,586 A | * 6/1994 | Ereren | 606/192 |
| 5,359,995 A | * 11/1994 | Sewell, Jr. | 600/207 X |
| 5,387,224 A | * 2/1995 | Semm | 606/191 |
| 5,400,773 A | * 3/1995 | Zhu et al. | 600/207 |
| 5,439,476 A | * 8/1995 | Frantzides | 606/192 |
| 5,496,345 A | * 3/1996 | Kieturakis et al. | 606/192 |
| 5,499,988 A | * 3/1996 | Espiner et al. | 606/114 |
| 5,520,609 A | * 5/1996 | Moll et al. | 600/204 |
| 5,588,951 A | * 12/1996 | Zhu et al. | 600/207 |
| 5,609,620 A | * 3/1997 | Daily | 607/105 |
| 5,695,514 A | * 12/1997 | Chin | 606/190 |
| 5,704,372 A | * 1/1998 | Moll et al. | 128/898 |
| 5,730,756 A | * 3/1998 | Kieturakis et al. | 606/190 |
| 5,735,791 A | * 4/1998 | Alexander, Jr. et al. | 600/37 |
| 5,799,661 A | * 9/1998 | Boyd et al. | 128/898 |
| 5,938,681 A | * 8/1999 | Pruitt, Jr. | 606/192 |
| 6,015,382 A | * 1/2000 | Zwart et al. | 600/207 |
| 6,036,640 A | * 3/2000 | Corace et al. | 600/207 |

FOREIGN PATENT DOCUMENTS

WO    WO-93/10850 A1 * 6/1993 ................. 600/207

* cited by examiner

*Primary Examiner*—Jeffrey A. Smith

(57) ABSTRACT

An inflatable manipulator for organ manipulation during surgery is disclosed. The system typically includes an inflatable balloon connected to an infusion source where the balloon is either coupled to a relatively rigid platform or fitted with a positioning structure such as a pocket. In open heart surgery, the platform is used to position and stabilize the balloon under the heart. In minimally invasive surgery, the balloon fitted with the pocket and can be rolled into a narrow configuration and inserted through a small incision using an insertion device. The insertion device can then be removed once the manipulator is in position. In use, the balloon of the manipulator is inflated by the infusion source thereby elevating and tilting the organ to the desired position for surgical access. Systems including multiple chamber manipulators each with a separate infusion source are also disclosed, as are combined methods for cooling organs during surgery and for using the manipulators to separate adhesions.

11 Claims, 16 Drawing Sheets

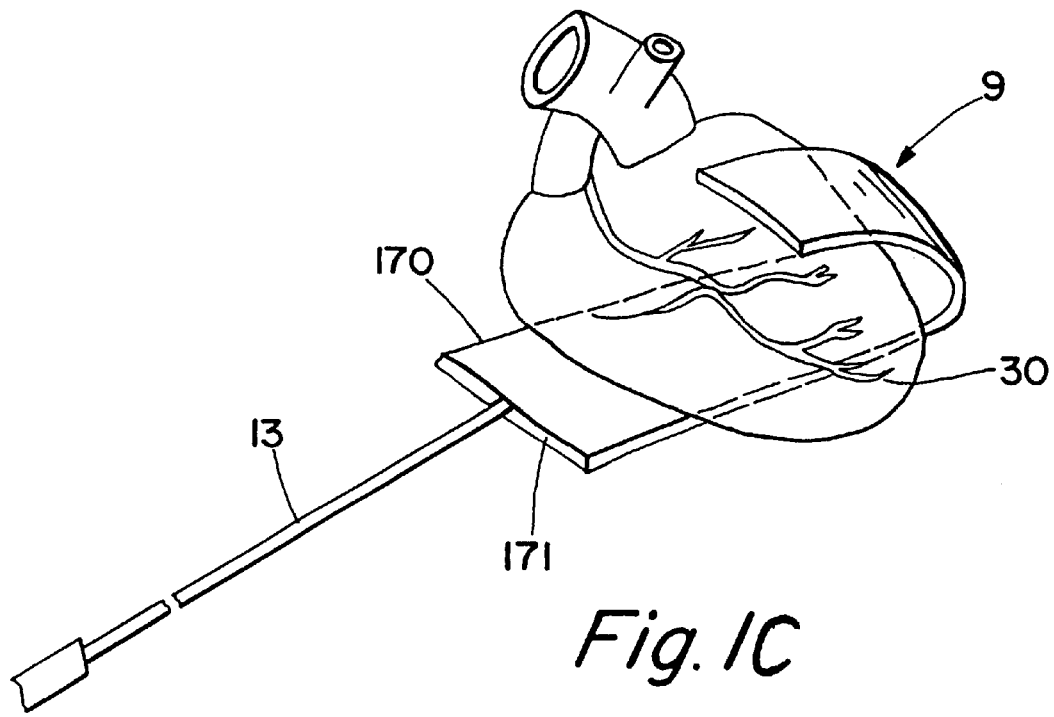
Fig. IC
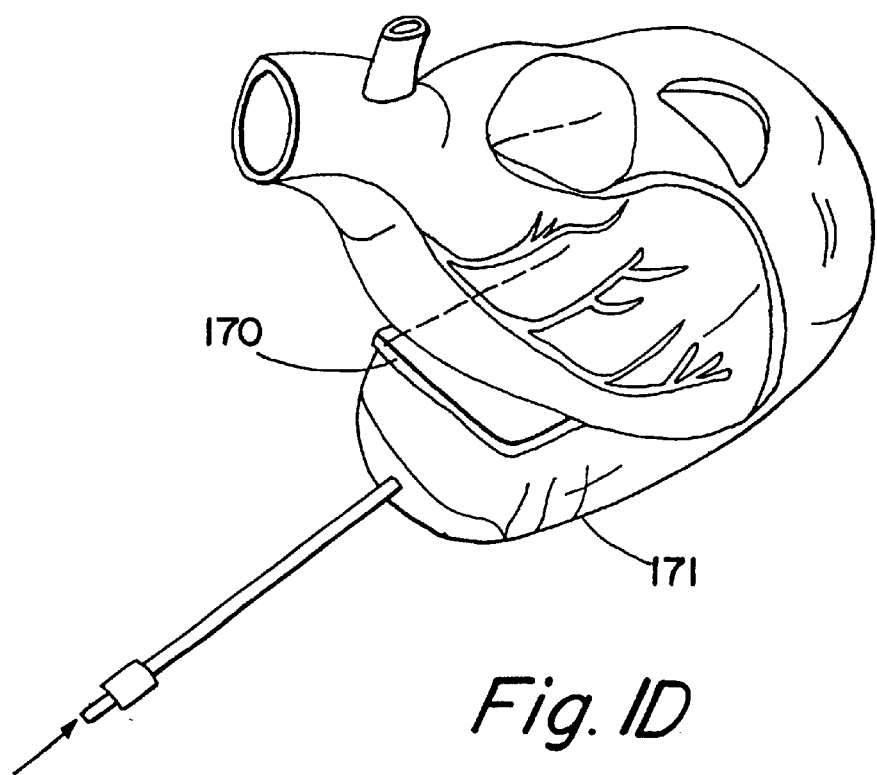
Fig. ID

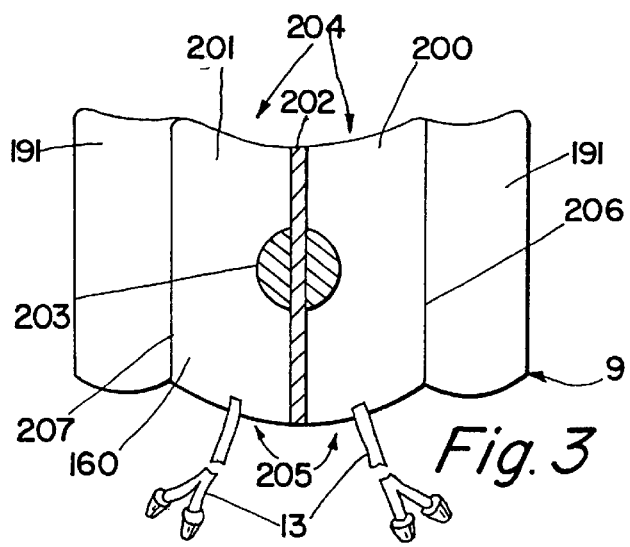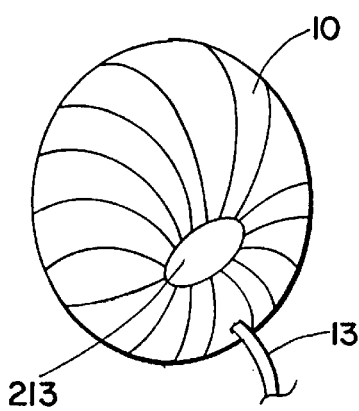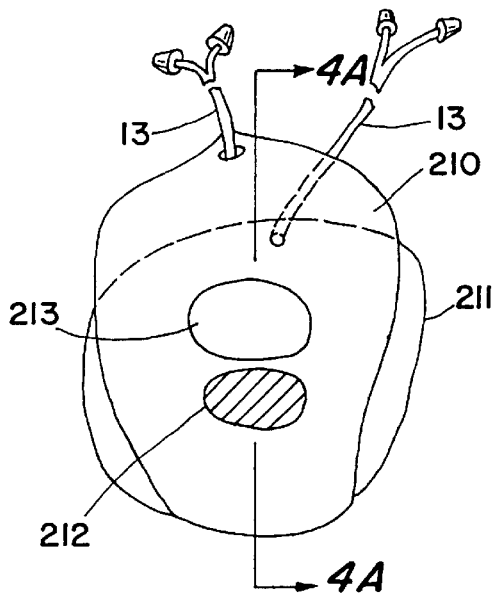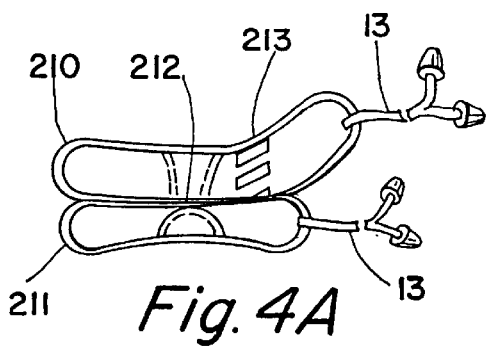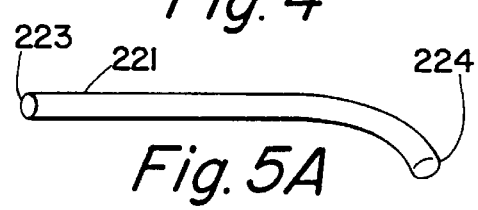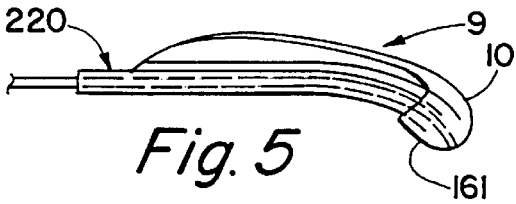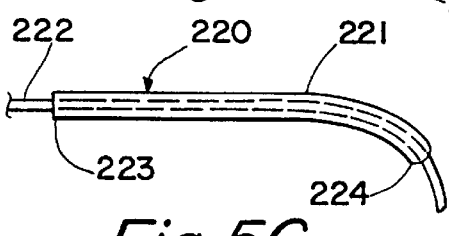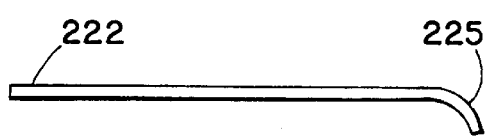

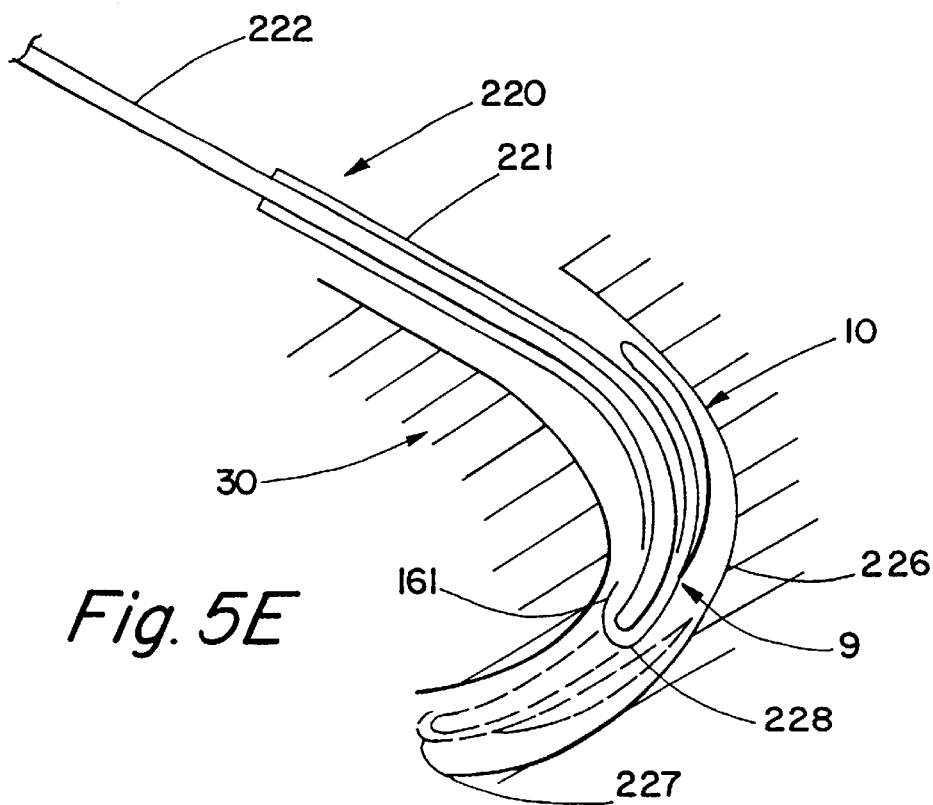
Fig. 5E
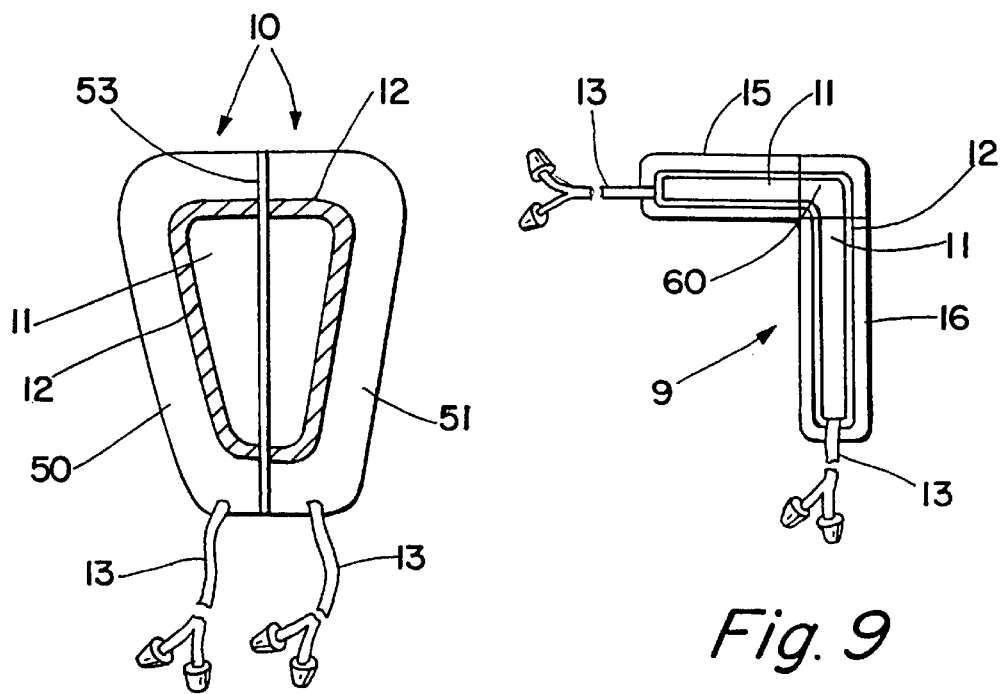
Fig. 8
Fig. 9

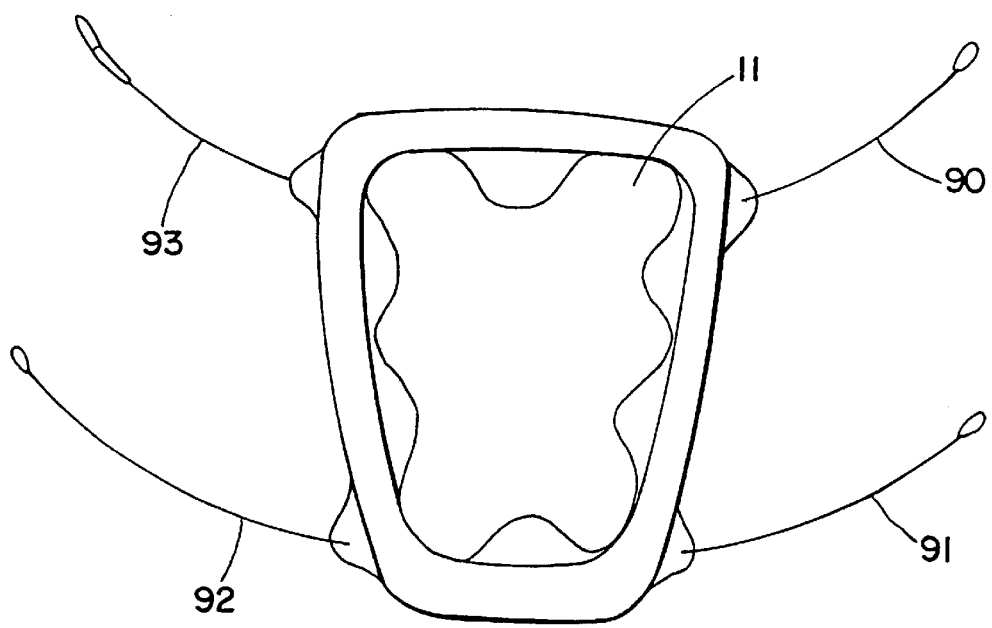
Fig. 11
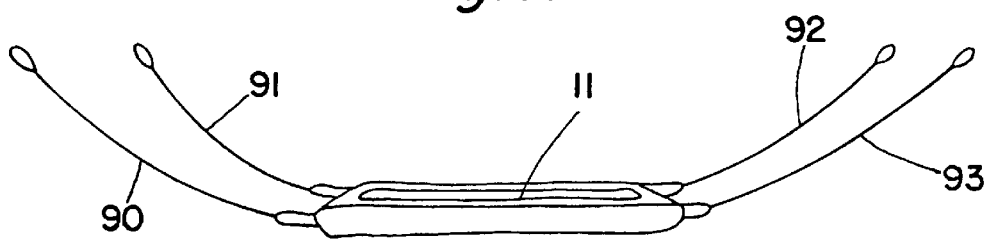
Fig. 11A
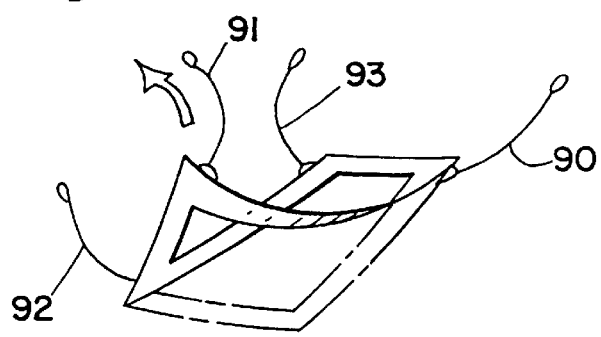
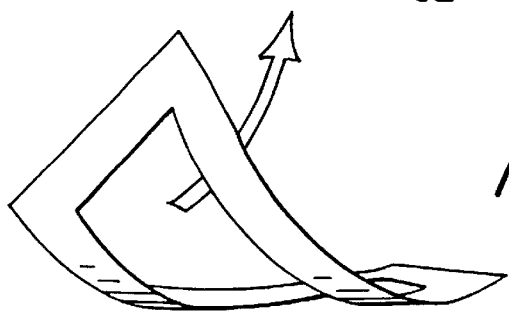
Fig. 11B
Fig. 11C

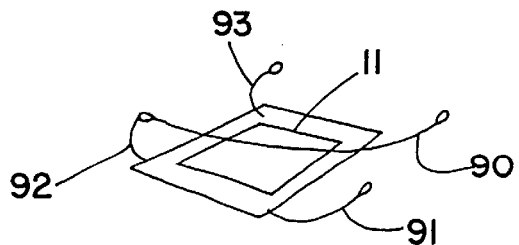
Fig. 11D
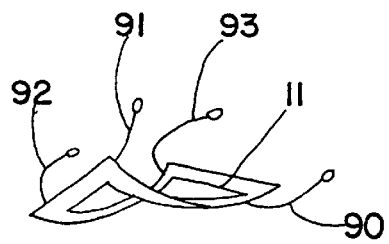
Fig. 11E
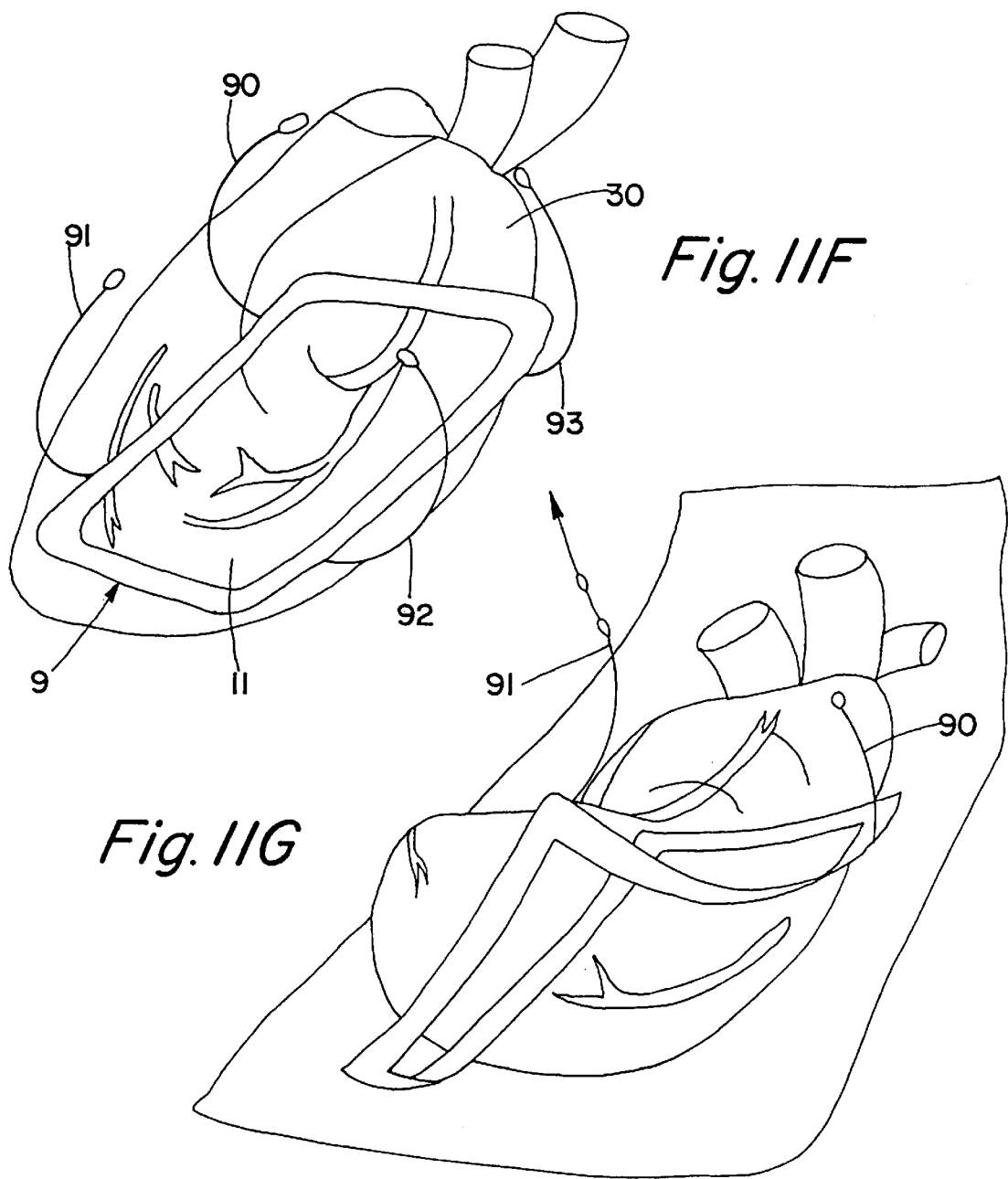
Fig. 11F
Fig. 11G

INFLATABLE MANIPULATOR FOR ORGAN POSITIONING DURING SURGERY

This is a continuation of application Ser. No. 08/951,799 filed Oct. 16, 1997, now U.S. Pat. No. 6,015,392, the contents of which are incorporated herein by reference in their entirety.

FIELD OF THE INVENTION

This invention relates to methods and apparatus to displace an organ from an adjacent anatomic structure and thereafter retract, orient, manipulate or stabilize it for further surgical procedures. The devices include an inflatable manipulator and various positioning and anchoring structures and tools to allow optimal placement of the manipulator in the desired anatomic location. Once in place, the manipulator is inflated to properly position the organ for surgery. The manipulator may optionally be used during surgery to dissect, cool or monitor the status of organs. The devices and methods disclosed herein are particularly suited for cardiac surgery.

BACKGROUND

The last half of the 20th Century has seen the birth and evolution of both open cardiac surgery as well as minimally invasive surgery (MIS) applied to a wide variety of procedures. Until recently, however, the two surgical specialties evolved largely independently. The complexity of the cardiac procedures, the potential for sudden and catastrophic complications, and the lack of effective tools to provide optimal surgical access inhibited development of MIS techniques.

Although open heart surgery has been employed to treat heart disease, most often it has been applied to reestablishing blood supply to the heart muscle itself. The principle objective is either to clear occluded arteries or to graft replacement vessels around the blockages. In the latter case, these coronary artery bypass graft (CABG) procedures are generally effective, but only for a limited time, usually a few to ten years. Traditional access to the heart requires a full sternotomy, forcible spreading of the sternal margins, and entry into the pericardium. Once inside the pericardium, manual manipulation of the heart is usually necessary to reach the blocked arteries. Currently, only makeshift manipulators and retractors are available for the surgeon to use in an attempt to position the heart to facilitate surgical access. Such crude tools include surgical gloves that have been inflated and tied off prior to placement under an organ and gauze pads that are also used to shim organs into position. However use of such primitive tools presents problems such as risk that the tools will inadvertently be left behind after the procedure is complete, risk of damage to the surface of the heart or pericardium during their placement and removal and lack of ability to perform real-time control of organ elevation and position. Other balloon devices have been disclosed that assist in removal of hollow organs and that move organs and other structures, such as the abdominal wall, away from the area of surgical interest. See Moll et al, International Application No. PCTUS92/04393; this and all other references cited herein are expressly incorporated by reference as if set forth herein in their entirety.

The interior surface of the pericardium itself is a delicate, serous membrane within which the heart slides freely. Any trauma to this surface, or to the heart itself, can subsequently cause adhesions to form, and therefore any means of manipulation or retraction must be very gentle. Reoperation within the pericardium often reveals evidence of previous traumatic manipulation, such as extensive adhesions between the heart and pericardium which must be released before further manipulation can be attempted. There is presently an unfulfilled need for more sophisticated devices that will permit atraumatic manipulation and stabilization of the heart and other organs and allow the surgeon to manipulate organ positioning from outside the surgical cavity.

Situations requiring more extreme manipulation create even greater intraoperative risk such as the likelihood that heart function will be impaired, or may even cease. The extent of motion required for such functional impairment to occur varies by individual and may be due to any of several causes, including kinking of the great vessels. If the heart ceases to function, the surgeon is faced with two choices, either (1) perform cardiopulmonary bypass (CPB), stopping the heart, or (2) lessen the manipulation until function is restored. The advantage of CPB is that it maintains apparent heart function to the rest of the body and provides opportunity for temperature control of the blood and cardioplegia being infused. However, a disadvantage is the risk of blood and organ damage. Moreover, prolonged bypass of the heart can damage heart tissue. However, it is thought that maintaining the heart in a hypothermic state may limit the degree of heart muscle necrosis. While other devices have been disclosed that cool the heart (see Daily, U.S. Pat. No. 5,609,620), these devices are not capable of simultaneously lifting and positioning the heart. On the other hand, stopping the heart has the advantage of allowing the heart to be emptied of blood, thus reducing its volume. Such volume reduction may, accordingly, allow more freedom for heart manipulation within the pericardium. Given these choices, it would seem most advantageous to work within a range of manipulation in which heart function is not compromised. Although such an outcome is attractive in some ways, it complicates the surgical procedure by presenting the surgeon with a beating heart upon which to complete very intricate anastomoses. The most advantageous solution, which has been unavailable heretofore, would be to not compromise heart function, yet provide a fixed surgical surface that is not affected by heart motion. It is clear that with current techniques and tools available, no one solution is without problems, and risk of trauma to the chest, and its resulting complications, is considerable. It is not therefore surprising that the search for better methods continues.

Early techniques designed to avoid some of the drawbacks of open heart surgery led to catheter techniques that open stenotic regions and reestablish blood flow without requiring arterial grafting. This advance was successful from the standpoint that it virtually eliminated trauma and reestablished blood flow quickly. However, some stenoses are difficult to treat using this technique, and its effectiveness is of limited duration. Such limitations led to the use of stenting in an effort to prolong patency. However, even with these advances, problems exist, and therefore, the search for other solutions still continues.

The middle ground of CABG surgery, performed through minimal incisions, is now becoming attractive. CABG surgery allows alternative approaches to a full sternotomy, the traditional incision used in open heart surgery, such as (1) a partial lower sternotomy, from the xiphoid process up to the second intercostal space, terminating in a transverse division to free the sternal margins, or (2) a mini-left thoracotomy, with partial removal of the fourth, left rib. Other choices are also in use or are currently being considered. As in open surgery, manipulation of the heart is still required and in fact, as incision sizes decrease, the nature and extent of this manipulation may change, and, accordingly, the difficulty may increase. In planning such a minimal incision, the surgeon must consider not only the desired manipulation of the heart itself for access to the coronary arteries, but must also consider optimal access to vessels which will be used to bypass the occluded arteries. The only tools available for such delicate cardiac manipulation and positioning are rigid manipulators with sharp contact points that can cause tissue trauma or primitive positioning tools discussed previously such as inflated gloves and gauze pads, which, in this procedure, are even more difficult to place and remove given the smaller incision size. Similar concerns apply to cardiac valve procedures where the heart must be positioned so that the appropriate surgical tools can reach the inner structure of the heart, as opposed to its surface.

In summary, it is clear the surgeon must weigh many issues in choosing the best access for a cardiac procedure. Such issues include: (1) patient-specific anatomy, condition and disease, (2) the requirements of the intended treatment, (3) the trauma likely to result, and (4) the likely risks of complications. Moreover, any procedure selected must align with the surgeon's own skill, knowledge, and comfort level. Any choice will involve some degree of compromise. However, the availability of better cardiac positioning and manipulation devices can expand the number of viable choices by reducing trauma to the patient and creating a surgical environment with better access and enhanced stabilization of the structures that are the subject of such delicate techniques.

Moreover, lack of such devices is an impediment to the advancement of surgical cardiac procedures. It is clear that incision size is trending downward, that future procedures may entail multiple incisions, and that, in time, "port" or cannula access may be the only technique used. As this reduced incision size evolves, the need for atraumatic manipulation and stabilization of the heart within the pericardium will increase markedly.

Although we have focused on the development of cardiac surgical techniques in the context of the evolution of the need for atraumatic positioning and manipulation devices, it is clear that need for such devices also exists in surgical procedures in other anatomic locations. For example, procedures that require lifting or positioning of solid organs including the liver and the spleen would be enhanced by the present invention.

Insofar as we are aware, there has been no disclosure of an inflatable manipulator that can atraumatically manipulate and stabilize organs for optional access during surgery, nor are such devices available. A need therefore exists for an inflatable organ manipulator which may include various enhancements for simultaneous organ cooling and monitoring and for dissecting adhesions, The following methods and apparatus more specifically can be used to place manipulators between the heart and the pericardium in order to manipulate and stabilize the heart's position and orientation, and to cool it during periods of prolonged bypass.

SUMMARY OF THE INVENTION

There are three common forms of manipulation of the heart within the pericardium in open surgery when access is by means of total sternomy. Perhaps the most common is elevation of the apex or ventricle end of the heart, in the anterior or forward direction. The second most common maneuver is elevation and medial rolling of the outer or lateral (obtuse) margin of the heart. Sometimes these two maneuvers are combined. Both maneuvers are directed at reaching the extremes of the left anterior descending artery and the circumflex artery on the left side of the heart. Neither motion generally requires elevation of the medial, superior corner of the heart. A less frequent maneuver is to lift and roll the medial or acute margin outwardly to access the extremes of the right coronary artery. With use of MIS access, the maneuvers may vary from open surgery techniques depending on the orientation and proximity of the surgical site to the incision or port.

The present invention relates to inflatable manipulators for organ positioning during surgery. One organ that may be so manipulated is the heart during MIS or open surgery.

In one embodiment, where MIS is to be performed, the manipulator comprises an inflatable balloon formed from one or more flexible or elastomeric sheets enclosing one or more chambers, each chamber in fluid communication with an infusion source, and the embodiment also includes a positioning structure. In this embodiment, the positioning structure is used to insert the manipulator into position between the organ and an adjacent structure. The deflated manipulator may be compressed or rolled into a narrow shape for insertion through the smaller incision typical of MIS. Once the manipulator is in the desired position, the balloon's chamber is inflated by infusing a liquid or gas through the infusion source until the balloon elevates and tilts the organ to the desired height and orientation. The surgical procedure is then performed on the organ. In one embodiment, liquid or gas cooled below normal human body temperature, 37° C., can be infused into the chamber to maintain the organ at a temperature below 37° C. and thus slow the rate of organ necrosis, for instance, during prolonged cardiac bypass procedures. In another embodiment, a sensor coupled to the balloon detects temperature, and temperature control of surfaces in contact with the balloon can be achieved. The sensor can be coupled to a computer or feedback system which provides information to a control device at the infusion source which then adjusts the temperature of the gas or liquid that is circulating through the balloon. The control device can be a pressure regulator or a mass flow controller coupled to the infusion source.

In one embodiment, the positioning structure is a pocket at the end of the balloon that is adapted to receive an insertion device. The pocket can be welded or fused to the end of the balloon. The insertion device includes a substantially tubular member curved at one end and a flexible rod that slidably inserts inside the tube and protrudes beyond the curved end of the tubular member. By sliding the flexible rod through the tube and placing it against the distal edge of the inside of the pocket, the manipulator can be advanced into the desired position inside the body cavity. Once the manipulator is in position, the insertion device is removed, leaving the manipulator in place and ready for inflation.

In certain embodiments, the positioning structure is a sheet that protrudes out from the balloon forming a flap. In some cases, the sheet is flexible and in other cases, where pushing the manipulator into place may be necessary, the sheet is relatively stiff. The sheet may be used to lift, slide or push the manipulator into position. The sheet may alternately be used to anchor the manipulator by placing the sheet under the organ upon which surgery is performed or a structure in the proximity of the organ. The sheet may be roughened to enhance traction on the organ or the adjacent structure. Such roughening can be accomplished by forming parallel ridges, dimples or blisters in the sheet or by coupling it to one-half of a hook-and-eye or Velcro® fastener pair. In one embodiment the sheet may be formed in the shape of a strap coupled along its long side to the outer surface of the balloon. Most of the coupling can be perforated so that once the manipulator is in the body cavity, the strap can be pulled away from the balloon along the perforated portion of the coupling and remain attached in the coupled region that is not perforated. This strap can then be used to further position the manipulator.

Another embodiment includes a plurality of parallel, tubular balloons joined at their outer surfaces to form a mattress. The balloons may be of equal diameter, or may be sized to result in a different vertical projection transverse to the general plane of the mattress. Although the balloons can be joined to form a single internal cavity, each balloon can be independently in fluid communication with a separate infusion source to allow independent control of the vertical projection of each balloon. In another embodiment, a large, flat balloon is internally fused in regions, or otherwise partitioned selectively, so that separate inflation of each chamber produces a contoured surface on the manipulator.

In certain embodiments, multiple balloons are arranged such that parts of each balloon overlap the other. These balloons can be fashioned out of more than two flexible sheets, or can be molded with internal partitions. The separate chambers can be connected to a single infusion source or can be connected to independent infusion sources. This embodiment is useful where the apex of the heart is to be lifted independently, the left or obtuse margin is to be lifted independently, or both the apex and the previously-described margin are to be lifted concurrently. In another embodiment, two balloons are formed in an inverted "L" shape and overlap at their common corner. This embodiment is placed such that the two "legs" of the "L" underlie the inferior and lateral regions of the heart, so that inflation of the inferior balloon would elevate the apex of the heart while inflation of the lateral balloon would roll the obtuse margin of the heart in a superior medial direction. When both balloons are inflated, a combined motion of apex lifting and medial rotation is achieved. Alternately, if the manipulator is placed with the balloon "legs" inferior and medial, access to the extremities of the right coronary artery can be achieved.

In another embodiment, where open cardiac surgery is to be performed, the manipulator comprises an inflatable balloon enclosing a chamber in fluid communication with an infusion source, and a relatively rigid platform which can be welded or otherwise fused at its perimeter, or near its center, to the balloon. In its simplest form, the balloon is a pillow-shaped, single-chamber balloon. The relatively rigid platform aids in insertion of the balloon under the organ to be lifted and in stabilizing the manipulator once it is in place. Once in position, the balloon is inflated through the infusion source to position the organ and surgery is performed.

Other embodiments include balloons that are partitioned by selectively fusing various regions of the balloon inner surface to produce more than one chamber where each chamber is in fluid communication with a separate infusion source. In other embodiments, two or more balloons are coupled to one another and can be coupled to the relatively rigid platform. By providing these combinations of chambers and balloons, various orientations of the organ can be achieved by selectively infusing each chamber or balloon with gas or liquid to the desired degree of inflation.

After inflation, balloons can assume a variety of shapes depending upon their construction including rectangular, spherical, oblong, tubular, triangular, toroid, annular or concave. The relatively rigid platform also be a variety of shapes including trapezoidal, triangular, square, rectangular, circular, oval and oblong. The relatively rigid platform may also be wedge-shaped and molded of polyurethane, silicone or medical grade foam and can include embedded balloons that expand away from the surface of the platform. This structure has the advantage of preventing balloon slippage during inflation and creating more precise positioning of the balloons on the platform during fabrication.

In other embodiments, various structures may be attached to the relatively rigid platform or to the outer surface of the balloon to aid in positioning or stabilizing. Such attached structures include flexible elongated members and sheets made of flexible or elastomeric material that serve as anchoring flaps. In one embodiment, the flexible elongated members may be fitted with a hole at the unattached end of each member. The hole may be used to attach the member to a flexible cord, including, but not limited to, suture material, so that the cord may be used to lift various edges of the relatively rigid platform to assist in properly positioning the organ or may be used to anchor the member to adjacent tissue. The members may be used to lift portions of the relatively rigid platform. In the embodiment where the attached structure is a sheet that extends out from the balloon forming a flap, such sheet may also be used to lift a portion of the balloon or the relatively rigid platform for better positioning. The sheet may alternatively be used to anchor the platform by placing such sheet under the organ or an adjacent structure in the proximity of the organ upon which surgery is performed. In one embodiment, a strap may be fashioned from the sheet and attached to the balloon or to the relatively rigid platform. In another embodiment, the attachment of the sheet or strap may be partially perforated, so that most of the sheet or strap may later be torn away and used for manipulation.

In another embodiment, a plurality of inflatable balloon pillars are coupled to a relatively rigid platform. The height of all balloons can be controlled by a single infusion source if uniform elevation of the organ is desired, or alternatively, each balloon can be controlled independently to give the surgeon intraoperative control of elevation of various regions of the organ.

One method of fabrication of balloons for this invention is the bonding or welding together of flat, polymeric sheets. Other methods include molding or dipping to form elastomeric balloons. Useful polymeric balloons can also be structured to change shape upon increasing inflation by selective yielding of portions of the balloons. For example, if balloons are constructed of multiple flat, flexible sheets of polymeric material, a weaker or thinner sheet will yield in preference to a stronger or thicker sheet. In this manner, a single chambered balloon might be flat during initial inflation, as constructed, and upon appropriate inflation, will assume a banana or crescent shape. The creation of the curved aspect can be accomplished during manufacturing, or, alternately during deployment and inflation within the patient. Similar results can also be achieved by blow molding chambers with eccentricity between the outer diameter and the inner diameter which results in unequal wall thickness.

By their nature, balloons can be designed to be quite hard and unyielding. However, for this invention, they are constructed in a manner that produces soft exteriors covering a large surface area, and are further designed to be compliant to accommodate the varying topography of the adjacent structures. Since sharp edges on the balloons may be trauma-producing, balloons fabricated from flexible sheets can be constructed by inverting the edges to avoid creation of sharp external edges that would result from welding or bonding where such external edges could come into contact with the heart or pericardium.

Since the objective of these heart manipulations is to present different areas to the surgeon for bypass surgery, it may be inconvenient if the balloon covers the particular surface segment which is the desired surgical site. Multiple chambered balloons are advantageous to overcome this problem, because they allow the surgeon to deflate part of the balloon at will to obtain the access needed, while still maintaining inflation in adjacent areas of the balloon for the necessary'support of the heart.

In order to further enhance the usefulness of the balloon designs outlined above, appendages or collateral features are advantageous. For example, roughening of the balloon outer surface can be used to increase friction of the balloon on the adjacent anatomic structure and prevent relative movement, for instance, between the heart and balloon or between the balloon and pericardium during surgery.

Adjacent sheets or straps made from a sheet can also be used to anchor the balloon in place. For example, if a flat sheet is attached to the balloon and trapped under the heart, the friction generated by the weight of the heart can be used to anchor the balloon. Alternately, if suture material or clamps are fastened to the sheet, these appendages can similarly be used to anchor the manipulator. In one embodiment, sheets, strings or straps are attached to the outer surface of the balloon and passed out of the body cavity through the incision'so that the sheets, strings or straps can later be used for manual manipulation, somewhat in the manner of the heart net devices used currently. These sheets, strings or straps can be attached to the outer surface of the balloon with perforated connection so that the sheets can be used during placement of the manipulator, and later, they can be partially or totally detached by pulling apart the perforations. In another embodiment, they may simply be left to pass out of the body through the incision during surgery and may later be used during retractor removal.

Prior to this invention, the common technique for organ positioning during surgery was to inflate and tie off surgical gloves, then place the inflated gloves under the organ. One of the many problems with this procedure was that degree of inflation had to be estimated before placement and could not be adjusted thereafter without removal of the glove. This invention allows real-time control of inflation and varying inflation techniques which can be of great assistance to the surgeon during certain procedures. For instance, in one embodiment, inflation can be applied with slowly increasing amplitude after placement of the manipulator under the heart to allow the surgeon to cease inflation before heart function is compromised and to signal the need for initiation of CPB. In this manner, limits of safe manipulation may be assessed and tailored to the needs of the individual patient. Suitable means of inflation include squeeze bulbs, syringes, or powered pumps. Inflation can be manually controlled by the surgical team, or mechanized for inflation in a predetermined manner or to a predetermined level.

In multiple chamber or multiple balloon constructions as outlined above in various embodiments, timing and sequencing of chamber filling can produce various compound actions, such as first lifting the obtuse margin of the heart, then subsequently rolling the heart medially. Such embodiments involving multichamber or multi balloon inflation sequencing can enhance the positioning maneuver compared to positioning achieved by a single chamber or a single fill alternative. In another embodiment, the lifting of a lower chamber can raise the heart to a position level with a lateral chamber which can subsequently be inflated, providing control which would otherwise be unavailable with a single chamber, single fill embodiment.

Use of real-time inflation also allows the possibility for sequencing balloon inflation and deflation to counteract the motion of a beating heart, leaving the surgical surface in a fixed position. Compensating for movement and providing a stable surface greatly enhances the surgeon's ability to perform delicate techniques. To accomplish this compensating movement, in one embodiment, open-loop or closed-loop feedback control is applied to chambers of support balloons where each balloon's inflation is individually controlled by computer in response to feedback from sensors such as a linear, variable differential transformer ("LVDT"), or other such devices which are attached to the heart along various axes. If, for example, the sensor is located near the point of anastomosis, the motion in that vicinity might be essentially stopped, making the anastomosis much easier even though the heart continues to beat.

The size of the incision and its position relative to the area of surgical interest within the body cavity affect the difficulty of placement of the manipulator in the desired location. The methods of the present invention include a variety of placement techniques. In certain cases, there may be room for the surgeon's hand to displace the heart in order to facilitate insertion of the balloon. In other cases, forceps or laparoscopic graspers can be used, such as a "Roticulator" grasper (United States Surgical Corporation). In the embodiments where the manipulator includes a relatively rigid platform, the rigidity of the platform will assist in insertion and further enhances reaching areas not accessible to the surgeon's hand, even if the platform is a foam structure.

In cases where the incisions are very small, or where cannulae are used, insertion may require the balloon be compacted and retained for insertion and placement purposes, then released prior to or during inflation. The methods of Kieturakis, et al., U.S. Ser. Nos. 08/483,293 and 08/484,208 are hereby incorporated by reference. For these small incision procedures, a particularly useful embodiment includes a balloon formed from one or more flexible sheets forming one or more chambers or one or more balloons each in fluid communication with an infusion source and also includes a positioning structure to allow placement via insertion device. In one embodiment, the positioning structure is a pocket provided at the distal end of the balloon adapted to capture the distal end of an insertion device, which device is then removed prior to or during inflation of the balloon. For example, see commonly assigned, co-pending application U.S. Ser. No. 08/815,398, now U.S. Pat. No. 6,004,340, which is hereby incorporated by reference.

In one embodiment, the insertion device is a substantially rigid tubular member which is curved at its distal tip to advance the manipulator as far as possible in the direction of desired insertion. A flexible rod slides Inside the tube and engages the pocket on the balloon. In one embodiment, the flexible rod is made of rubber and in another embodiment it is made of Nitinol. The rod extends slightly beyond the tube to engage the pocket, and the balloon is staged along the tube and rod. In positioning manipulators for cardiac surgery, the insertion device and manipulator are advanced to the point where the curvature of the tube is at the maximum heart curvature, and the rod is then advanced relative to the tube, carrying the balloon further around the curvature of the heart. When the balloon is properly positioned, the rod is withdrawn into the tube, and the rod and tube withdrawn from the incision. The withdrawal of the insertion device can be concurrent with initiation of balloon inflation. The reach of the insertion device can be further extended if the rod is itself curved where it extends beyond the tip of the tube.

In one method, the manipulators are used to release adhesions between adjacent tissue structures, such as adhesions that may form between the heart and the pericardium. Such release can be accomplished either by using the manipulator to stretching the adhesions to facilitate exposure for sharp dissection, or by using the manipulator to actually pull apart adhered layers. This latter method can only be used where there is no danger of tearing in an unintended structure.

BRIEF DESCRIPTION OF DRAWINGS

Reference is now made to a brief description of the drawings, which are intended to illustrate an inflatable manipulator for use herein. The drawings and detailed description which follow are intended to be merely illustrative and are not intended to limit the scope of the invention as set forth in the appended claims.

FIG. 1C depicts another embodiment of FIG. 1B, where the deflated crescent-shaped manipulator has been positioned behind the heart.

FIG. 1D shows the embodiment of FIG. 1B in an inflated condition positioned behind the heart.

FIG. 3 depicts a two-chambered manipulator with a fused area in the center and with two flexible sheets attached to the sides.

FIG. 4 depicts a toroid manipulator with a center hole and a fused area just below the center hole, where the fused area is further fused to a second manipulator attached behind the first.

FIG. 4A is a lateral view of the embodiment of FIG. 4 along line 4A—4A.

FIG. 4B is a single-chamber toroid-shaped manipulator, where the opening is laterally displaced and shows the different degrees of lift on each side of the opening.

FIG. 5 is a cross-section of an insertion device fitted into a pocket positioning structure of a balloon.

FIG. 5A shows the substantially rigid tubular member of the insertion device.

FIG. 5B shows the rod of the insertion device.

FIG. 5C shows the rod inserted into the substantially rigid tubular member.

FIG. 5D shows another embodiment of FIG. 5B where the rod is curved at one end.

FIG. 5E shows a cross-section of an insertion device fitted into a pocket positioning structure of a balloon, where the insertion device and the balloon have been positioned between the heart and inner layer of the pericardium.

FIG. 8 depicts a top elevation of another embodiment where the balloon has two chambers.

FIG. 9 depicts a top elevation of an embodiment where there are two balloons coupled to one another to form an angle.

FIG. 11 depicts another embodiment of the invention where the embodiment of FIG. 6 has been fitted with flexible elongated members.

FIG. 11A shows the lateral view of embodiment of FIG. 11.

FIG. 11B shows the embodiment of FIG. 11 where one flexible elongated member has been pulled to lift a corner of the manipulator.

FIG. 11C shows the embodiment of FIG. 11B from a different view.

FIG. 11D shows the embodiment of FIG. 11 manipulated by pulling the flexible cords cross-diagonally.

FIG. 11E shows the embodiment of FIG. 11 manipulated by pulling the flexible cords to lift a particular corner.

FIG. 11F shows a bottom elevation of the embodiment of FIG. 11 positioned behind the heart.

FIG. 11G shows the embodiment of FIG. 11 where the flexible cords have been manipulated to roll the lateral margin of the heart medially to access portions of the left coronary artery that run along the dorsal side of the heart.

DETAILED DESCRIPTION

Figure 1A:
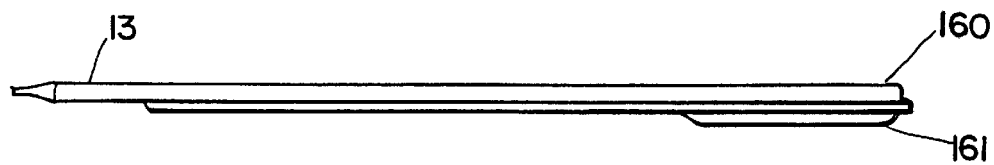
FIG. 1A shows a lateral cross-sectional view of the embodiment of FIG. 1 in a deflated condition, shown through section line 1A—1A.
Figure 1:
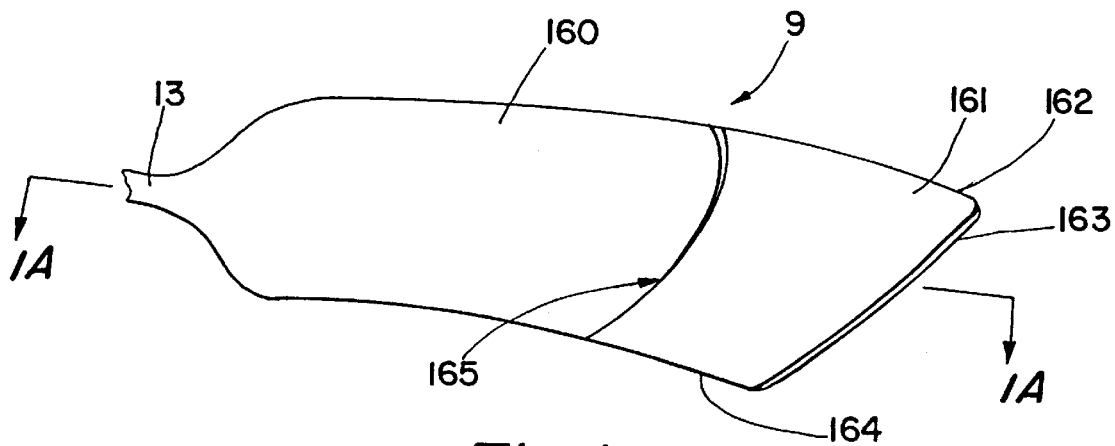
FIG. 1 depicts the bottom elevation of an embodiment, where the balloon is formed from a flexible sheet and is fitted with a pocket positioning structure adapted for an insertion device to position the balloon.

FIG. 1 depicts one embodiment where the inflatable balloon of a manipulator 9 is formed from a flexible sheet 160 enclosing a chamber which is in fluid communication at its proximal end with an infusion source 13 and the manipulator includes a positioning structure 161. This embodiment is suited for minimally invasive surgery ("MIS"), because a compacted, flexible retractor may more easily fit through a smaller incision. The embodiment uses a positioning structure to aid in positioning the manipulator. In one embodiment, shown in FIG. 1, the positioning structure is a sheet 161 attached at the distal end of the manipulator to form a pocket. The sheet is coupled to the balloon along three edges 162, 163, and 164 and is open along a fourth edge 165 so that the opening of the pocket 165 faces the proximal end of the manipulator where the infusion source 13 lies and is adapted to receive an insertion device. FIG. 1A is the lateral view of a deflated manipulator of the embodiment of FIG. 1 through section line 1A—1A.

Figure 1B:
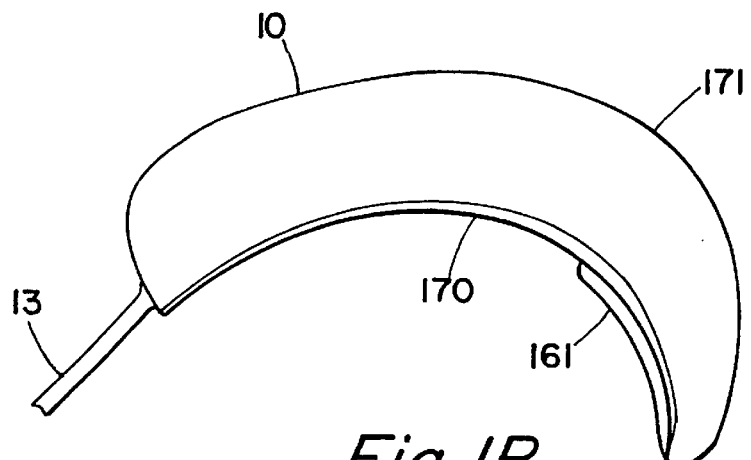
FIG. 1B shows a lateral view of an embodiment of FIG. 1 where the balloon has been formed from two flexible sheets of different thickness creating a crescent-shaped manipulator on inflation.
Figure 1E:
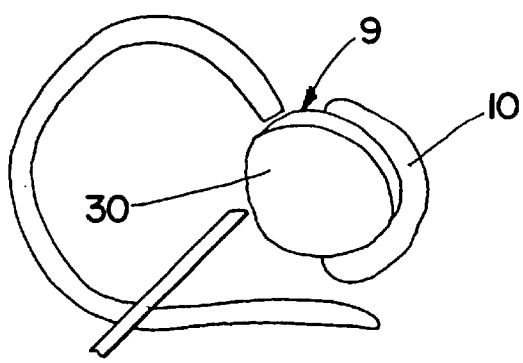
FIG. 1E shows a cross-section of the device of FIG. 1 positioned around the heart.
Figure 1F:
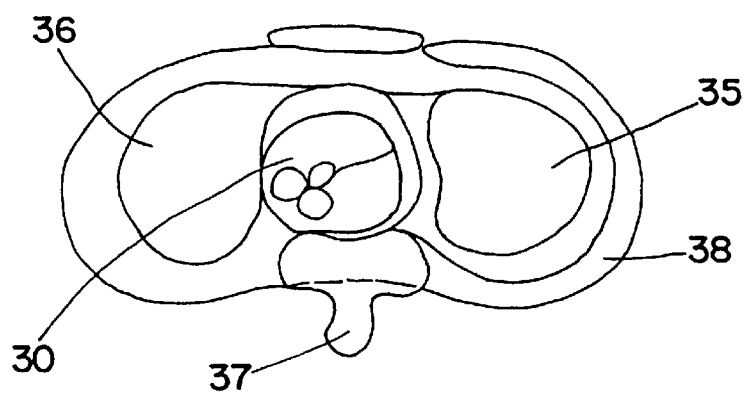
FIG. 1F shows a cross-section of the mid-thoracic area.
Figure 1G:
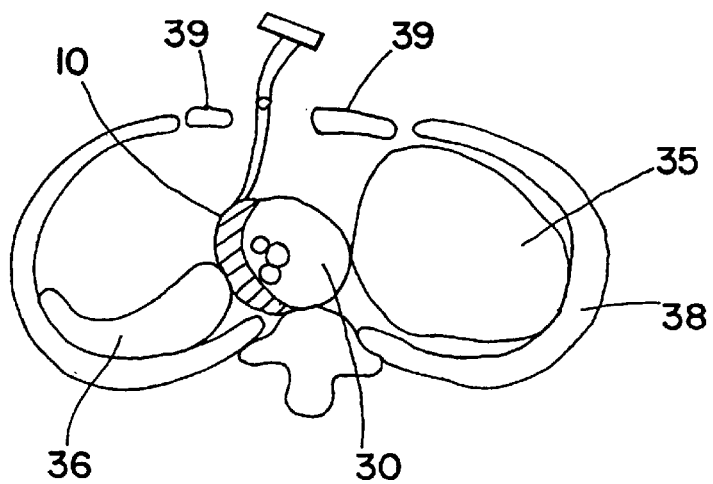
FIG. 1G shows a cross-section of the mid-thoracic area with the manipulator wrapped around the heart.

In another embodiment, the manipulator can be formed from a plurality of flexible sheets. FIG. 1B shows an embodiment formed from two flexible sheets of varying thickness. One sheet 170 is thicker than the other sheet 171, so that upon inflation, the balloon 10 ultimately forms a crescent-shape, curved in the direction of thicker sheet 170. In another embodiment, the manipulator is formed from a plurality of elastomeric sheets, where one sheet is more elastic than another and the balloon forms a crescent shape upon inflation, curved in the direction of the less elastomeric sheet. FIG. 1C and FIG. 1D show how the crescent-shaped embodiment is used to wrap around an organ, in this case the heart 30. FIG. 1C shows the embodiment before inflation and FIG. 1D shows the embodiment after inflation. This embodiment is useful in procedures where the heart must be rolled and stabilized. This embodiment can be placed behind the heart 30 endoscopically as shown in FIG. 1E, FIG. 1F and FIG. 1G. FIG. 1F is a cross-section of the mid-thoracic area showing a thoracic vertebra 37, the right lung 35, the left lung 36, and the rib cage 38. When inflated, the manipulator wraps around the backside of the heart forcing it ventrally and stabilizing it during the procedure. FIG. 1G shows an inflated balloon 10 and a deflated left lung 36 with the manipulator extending through a split in the sternum 39.

Figure 2:
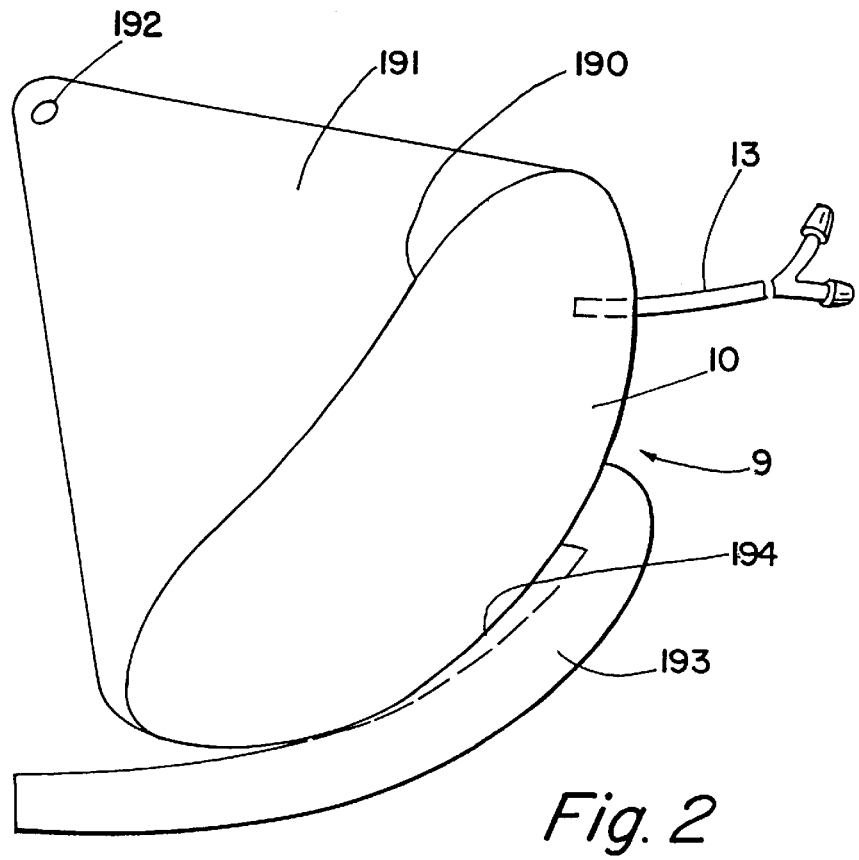
FIG. 2 depicts a top elevation of another embodiment, where a single-chamber balloon is coupled on one end to a sheet for anchoring the manipulator into position, such sheet provided with a hole, and coupled on the other end along a partially perforated edge to a strap.

In another embodiment shown in FIG. 2, the balloon 10 is coupled along a line 190 to a positioning structure that is a sheet 191 that forms a flap adapted to anchor the manipulator 9. The sheet can be partially detachably coupled to the balloon. In certain embodiments, the sheet can be placed under the heart to anchor the manipulator in place. In one embodiment, the sheet is relatively stiff and is used to push the balloon under the organ. In another embodiment, the sheet 191 can be fitted with a hole 192 to attach a flexible cord or to anchor the manipulator using suture material. A strap 193 can also be fashioned from a sheet and partially detachably coupled along a line 194 so that after placement of the manipulator, the strap can be partially torn away from the balloon and used to lift the manipulator. In certain embodiments, the sheet is partially perforatably coupled to the balloon.

Figure 2A:
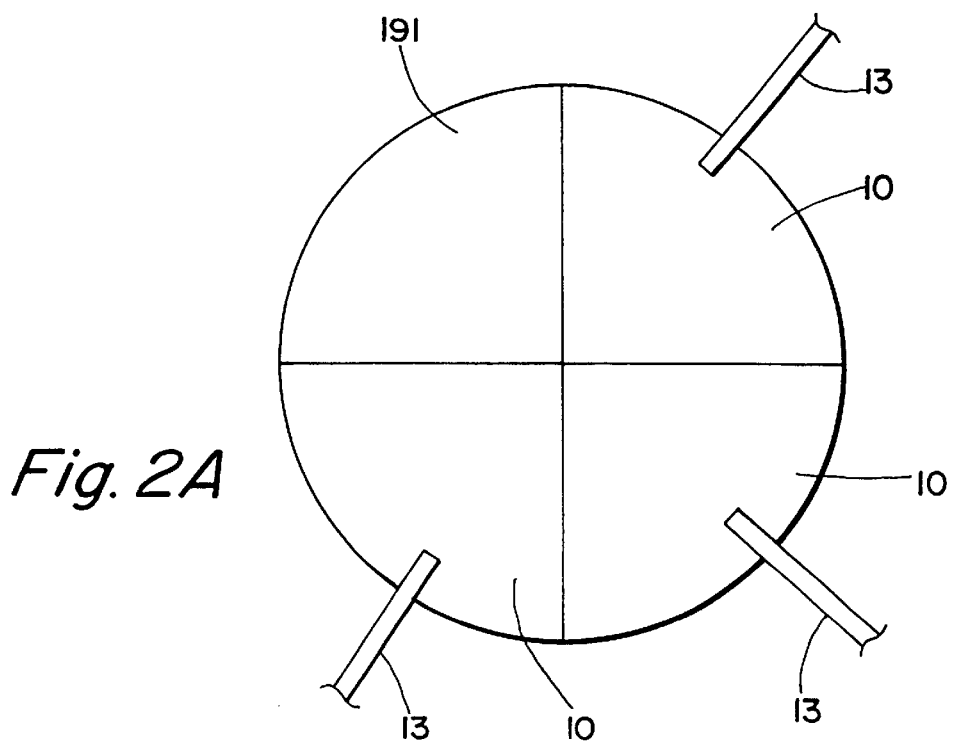
FIG. 2A depicts a top elevation of another embodiment, where a multi-chamber balloon is coupled to a sheet in the upper left corner.

FIG. 2A depicts another embodiment where three balloons 10 are coupled to one another and to a sheet 191 that serves as an anchor flap. In another embodiment, the sheet is relatively stiff and is adapted to push the manipulator under the organ.

FIG. 3 depicts another embodiment where the flexible sheet is partially coupled to itself to form a plurality of chambers. The flexible sheets 160 of the manipulator 9 have been fused along a center line 202 that runs from the proximal end to the distal end of the balloon to form two chambers 200 and 201 each with a separate infusion source 13. This embodiment also has an area 203 where regions of the inner surface of the flexible sheets forming the balloon have been fused together so that upon inflation, the area above the fused area 203 forms a recess in which an organ can be cradled. The fused area may be replaced by a hole, and either the fused area or the hole may be located or sized to control the vertical elevation of various regions of the torus so formed. The distal end 204 is concave to permit passage of the great vessels. The proximal end 205 is convex to assist in elevation of the apex of the heart. The flat sides 206 and 207 are coupled to sheets 191 that can serve as flaps for manipulation or anchoring.

FIG. 4 depicts another embodiment wherein two manipulators 210 and 211 have been coupled to one another. The top manipulator 210 is toroid in shape when inflated and has a fused area 212 wherein regions of the balloon inner surface of the top manipulator 210 have been coupled to one another to create a recess after inflation. Such coupling can occur by fusing the regions together. The bottom manipulator 211 has a similar area 212 where regions of the balloon inner surface of the bottom manipulator 211 have been fused to one another. The top and bottom manipulators have additionally been fused to one another at area 212. The top manipulator 210 has an opening 213 where a fused area has had a portion of the fused material removed. This area 213 is the hole in the toroid after inflation. In another embodiment, the opening or recess can be displaced laterally to create varying amounts of lift in the top manipulator 210 upon inflation. FIG. 4A is a lateral cross-sectional view of the embodiment of FIG. 4 through section line 4A—4A. FIG. 4B shows a single-chamber toroid manipulator where the opening 213 has been laterally displaced in the balloon 10 and demonstrates the varying degrees of lift on either side of the opening as a result of such lateral displacement.

The embodiment that includes a pocket as a positioning structure requires a insertion device for positioning as depicted in FIG. 5. Here, the manipulator 9 is fitted with a positioning structure that is a pocket 161 adapted to receive the insertion device 220. The insertion device includes a substantially rigid tubular member 221, straight on a first end 223 and substantially curved on a second end 224, as shown in FIG. 5A, and a flexible rod 222, as shown in FIG. 5B, where the rod is of greater length than the tubular member and is adapted to be slidably inserted into the first end of the tubular member as shown in FIG. 5C. FIG. 5C also shows that the rod is shaped to protrude beyond the second end 224 of the substantially tubular member. FIG. 5D shows a flexible rod with a curved distal end 225 to facilitate manipulator placement. FIG. 5E shows the insertion device 220 fitted inside the pocket 161 of a manipulator 9 where the balloon 10 is deflated and the flexible rod 222 is being pushed through the substantially rigid tubular member 221 against the end of the pocket 228 to advance the end of the pocket, and thus the manipulator, to point 227 between the heart 30 and the pericardium 226. The insertion device is then removed through the surgical opening, leaving the manipulator in place.

Figure 6:
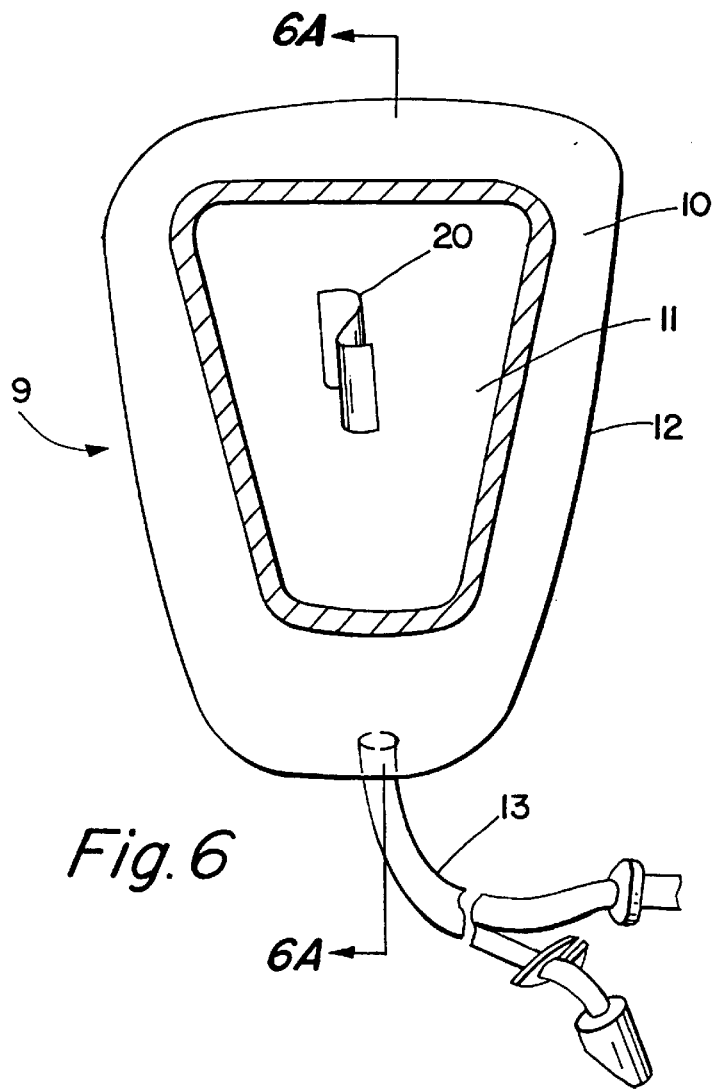
FIG. 6 depicts a top elevation of one embodiment of the present invention, where the manipulator includes a relatively rigid platform and a height limiter.
Figure 6A:
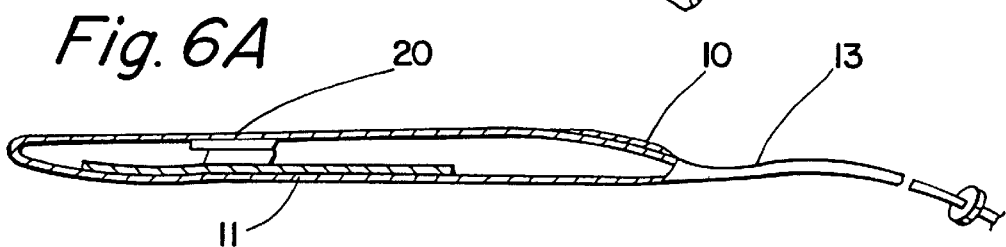
FIG. 6A shows a lateral cross-sectional view of the embodiment of FIG. 6 in a deflated condition, shown through section line 6A—6A.
Figure 6B:
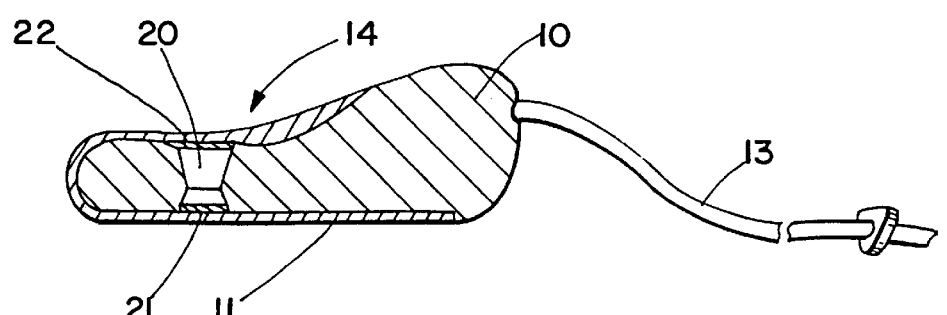
FIG. 6B is the embodiment of FIG. 6A in an inflated condition.
Figure 7:
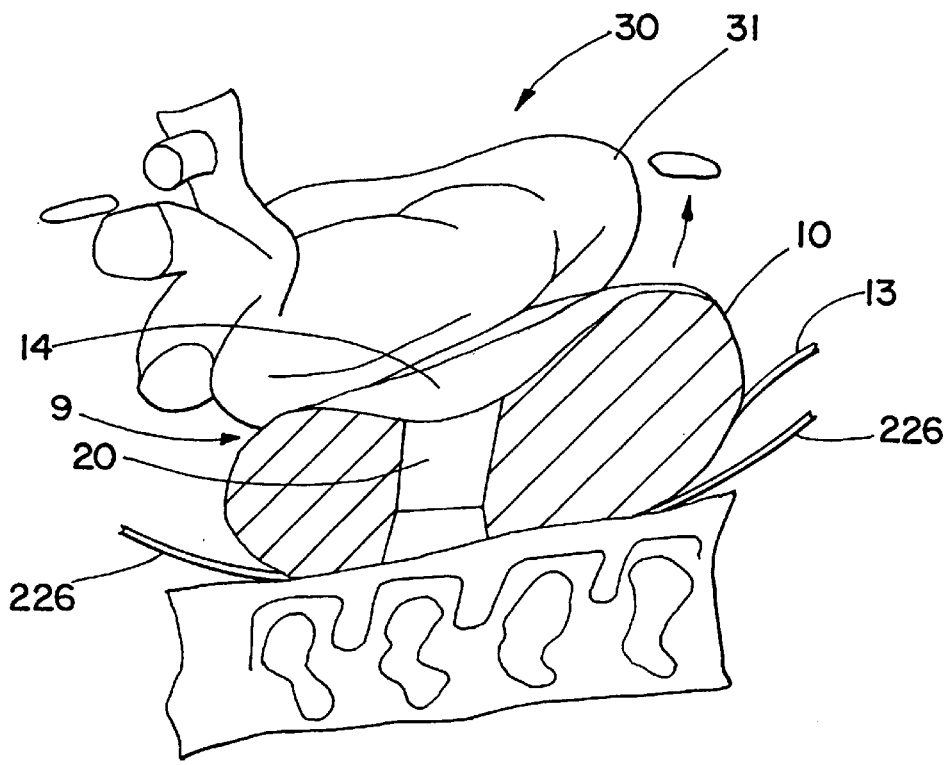
FIG. 7 depicts the embodiment of FIG. 6 in a lateral cross-sectional view, where the manipulator has been positioned between the dorsal surface of the heart and the pericardium, and, in its inflated condition, elevates the apex of the heart.
Figure 7A:
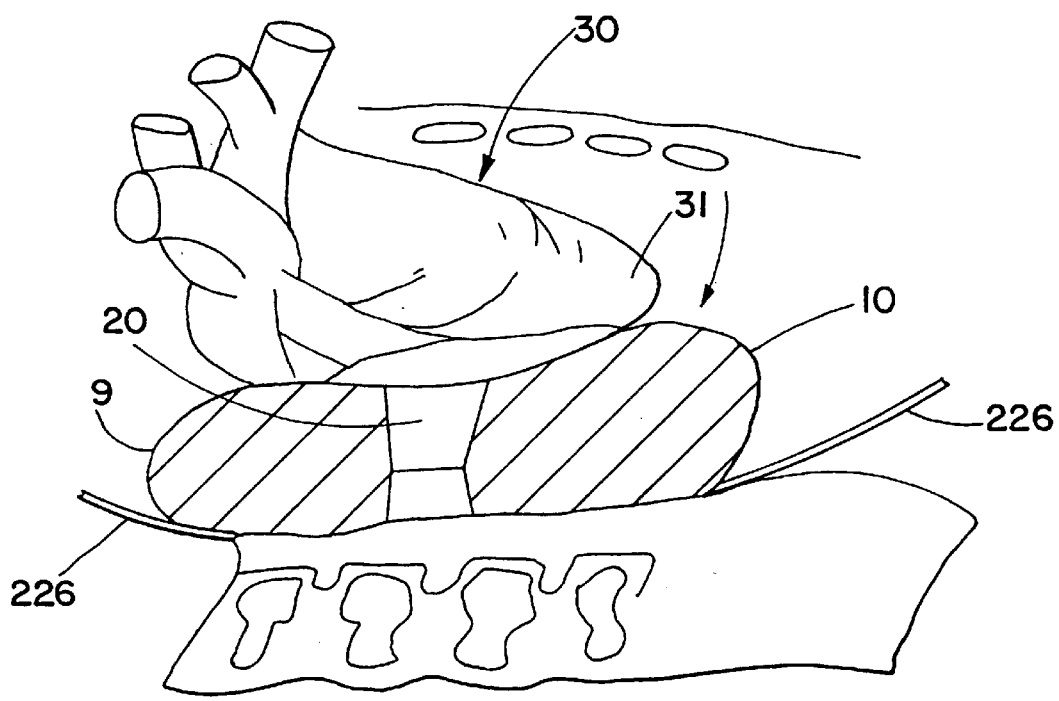
FIG. 7A is the embodiment of FIG. 7 in a deflated condition.

In another embodiment, as depicted in FIG. 6, the manipulator includes a relatively rigid platform 11, an inflatable balloon 10 coupled to the relatively rigid platform along a line 12, and an infusion source 13 in fluid communication with the proximal end of the balloon. The inflatable balloon encloses a chamber. In certain embodiments, the manipulator includes a height limiter 20. The balloon is made of a flexible sheet that allows it to be inflated when gas or fluid is passed through the infusion sources. In one embodiment, the flexible sheet is polyurethane. In certain embodiments, the flexible sheet is an elastomeric sheet. The manipulator is shown in a lateral cross-sectional view in a deflated condition in FIG. 6A, and the same view is shown in an inflated condition in FIG. 6B. When the balloon 10 is in a deflated condition as shown in FIG. 6A, the height limiter 20 is in a collapsed condition. When the balloon 10 is in an inflated condition as shown in FIG. 6B, the height limiter 20 is in a fully expanded condition. The height limiter has a first end 21 coupled to the inner surface of the balloon in the region where the balloon contacts the relatively rigid platform and a second end 22 coupled to the inner surface of the balloon in the region where the balloon expands away from the relatively rigid platform. In the expanded condition, the height limiter creates a concave surface or recess 14 in the region of the balloon to which it is coupled. The height limiter can also be used to create a recess in manipulator embodiments which do not include a relatively rigid platform. In another embodiment, the height limiter is displaced laterally from the center of the balloon to change the location of the recess and to create areas of varying lift. FIG. 7 shows the manipulator 9 of FIG. 6 positioned between the dorsal surface of the heart 30 and the pericardium 226. The heart 30 rests in the recess 14 of the manipulator. In FIG. 7, the balloon 10 has been inflated so that the apex of the heart 31 is elevated to its desired surgical position. FIG. 7A shows the balloon slightly deflated, illustrating the descent in the position of the apex of the heart 31 as a result of the deflation. The manipulator can similarly be used to position other organs to facilitate surgical access.

In certain embodiments, the gas or liquid circulated in the chamber through the infusion source may be maintained at a temperature less than 37° C., the temperature of the human body, in order to maintain the tissue that the balloon contacts in a hypothermic condition. Such cooling can help preserve tissues during surgery and slow the rate of beating of the heart. The concept of constant infusion of saline solution into the balloon is a means of preserving heart tissue during coronary bypass surgery. Prolonged bypass of the heart can potentially damage heart tissue, and it is believed that maintaining tissue at a hypothermic condition during such surgery will limit heart muscle necrosis.

In another embodiment the balloon may have more than one chamber as depicted in FIG. 8. The balloon 10 has been coupled to a relatively rigid platform 11 along a line 12 and regions of the inner surface of the balloon have been coupled together along a center line 53 to form two chambers, 50 and 51. Each chamber is in fluid communication with a separate infusion source 13. In certain embodiments, the center line 53 is fused or welded. A manipulator of this embodiment will form a recess upon inflation along the center line 53 to cradle an organ. Since each chamber of the manipulator can be independently inflated to the desired height, the organ can be tilted from side to side to facilitate surgical access.

In another embodiment, the manipulator may be formed from two or more balloons coupled together as depicted in FIG. 9. The manipulator 9 has two balloons, 15 and 16, which overlap in area 60 where one balloon 16 lies on top of the other balloon 15 to form an angle. The balloons are coupled to a relatively rigid platform 11 along line 12. In the overlap area 60, the lower balloon 15 is coupled to the relatively rigid platform and the bottom of the upper balloon 16 is coupled to the top of the lower balloon 15 in area 60. Each balloon is in fluid communication with an infusion source 13. Since each balloon may be individually inflated to varying degrees, the organ that the manipulator supports can be tilted and elevated to the desired surgical access position.

Figure 10:
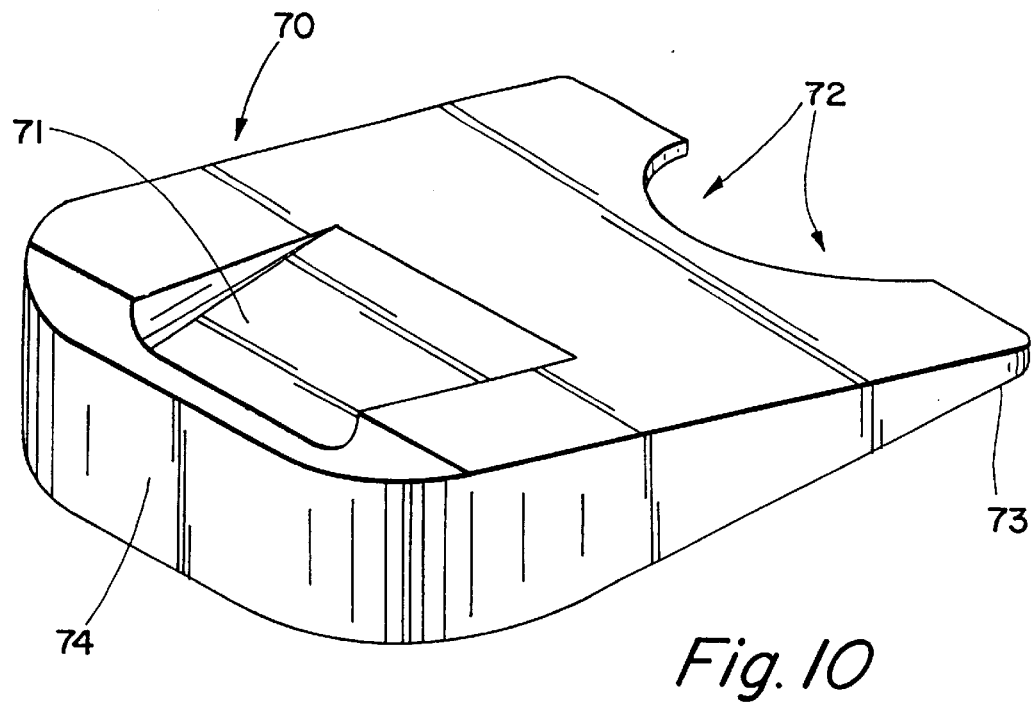
FIG. 10 shows a wedge-shaped relatively rigid platform of a manipulator in a deflated condition.
Figure 10A:
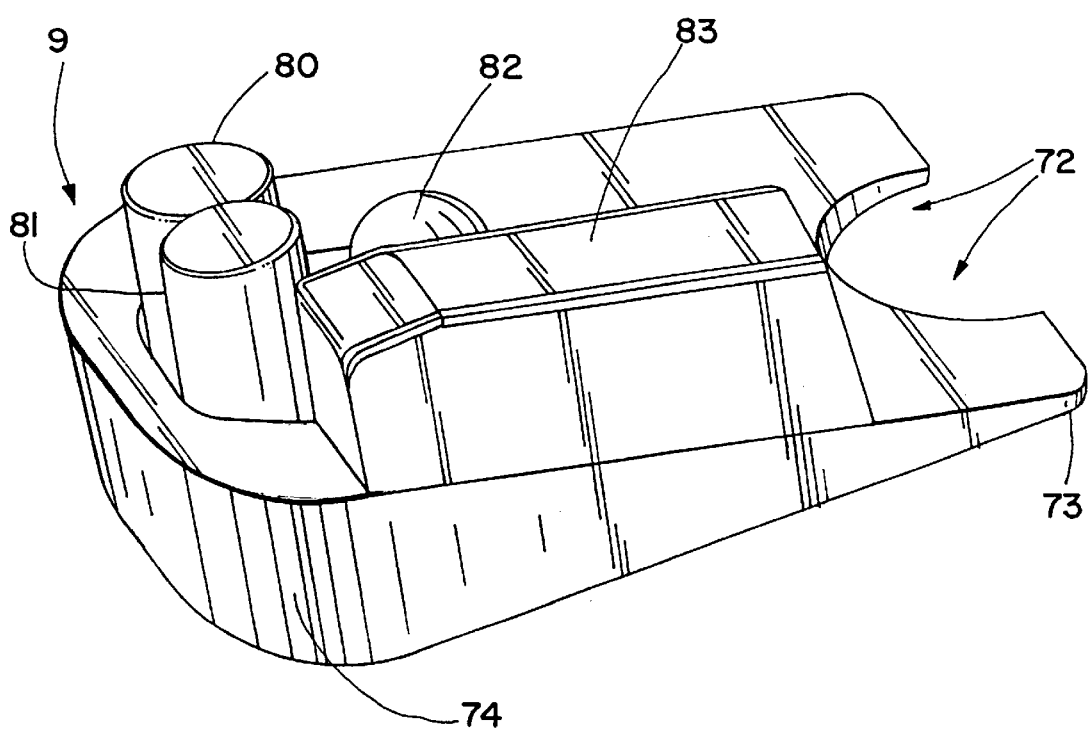
FIG. 10A shows the manipulator of FIG. 10 in an inflated condition.
Figure 10B:
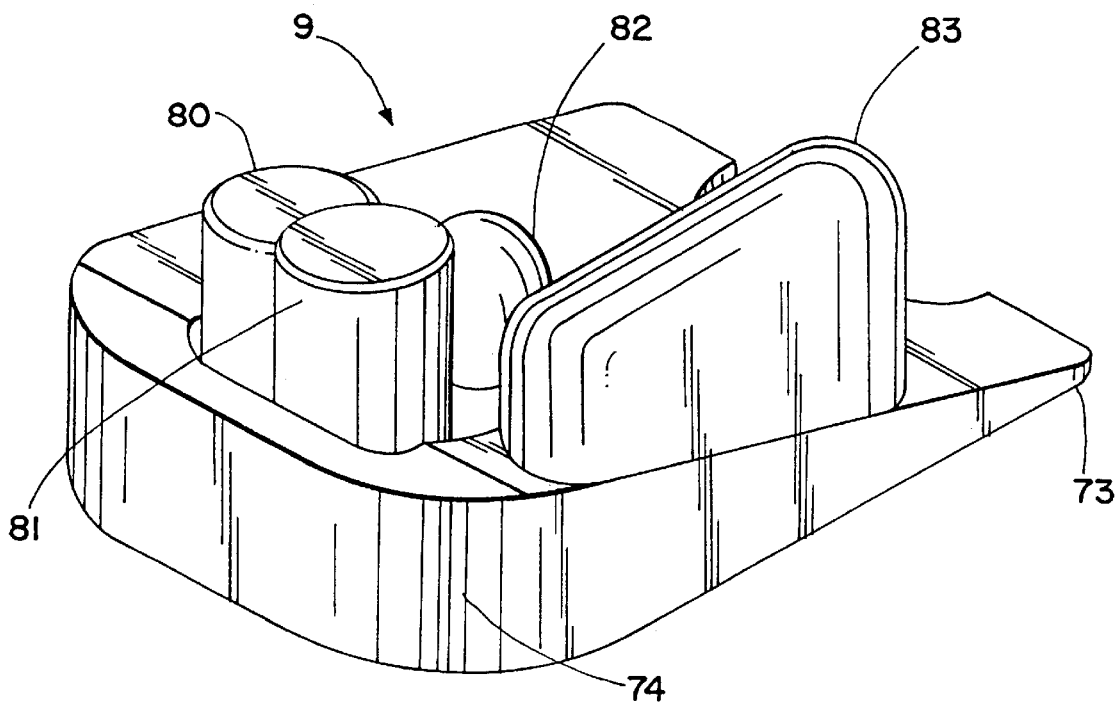
FIG. 10B shows the manipulator of FIG. 10 in an inflated condition from a different view.
Figure 10C:
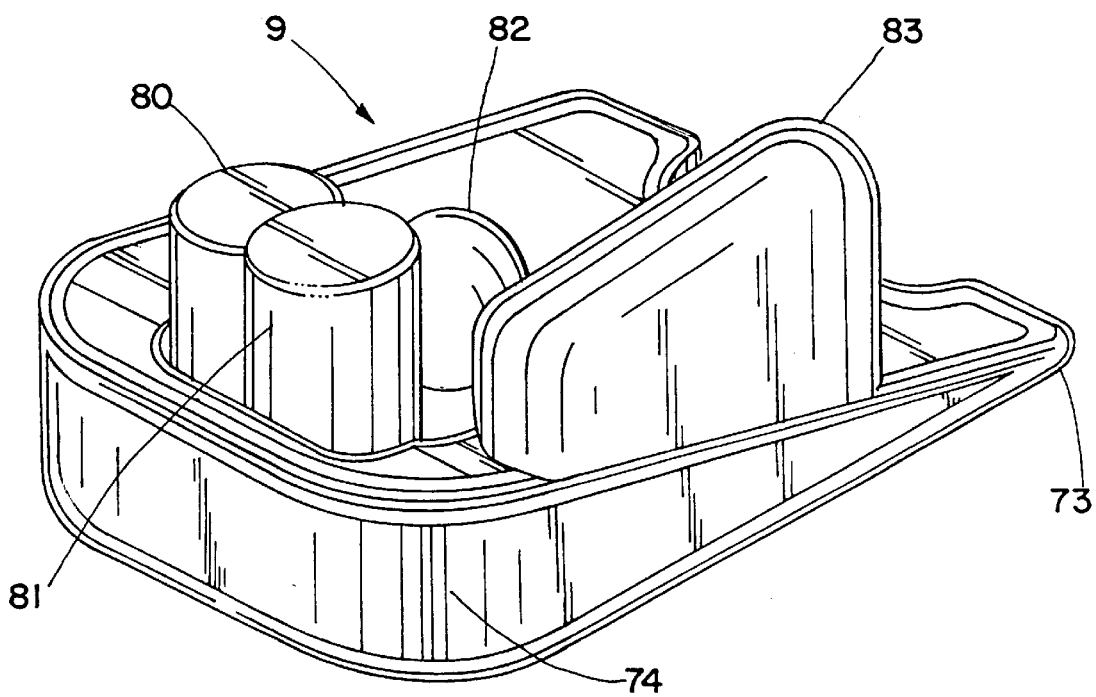
FIG. 10C shows the manipulator of FIG. 10A with soft, rounded edges.

In another embodiment, the relatively rigid platform 70 is wedge-shaped as shown in FIG. 10, with a first end 73 that is thinner than the second end 74. In one embodiment, the wedge-shaped platform is molded. In certain embodiments, the platform has a recess 71 in which the organ rests. In another embodiment for use in cardiac surgery, the first end 72 is concave to allow passage of the aorta, the pulmonary trunk and the superior vena cava (the "great vessels" of the heart). In one embodiment, the relatively rigid platform is polyurethane; in another embodiment, it is silicone; and in yet another embodiment, it is medical grade foam. In one embodiment, the wedge-shaped relatively rigid platform has a plurality of balloons 80, 81, 82 and 83 embedded in it. These balloons are molded to the top surface of the relatively rigid platform and are expandable away from the surface. The molded embodiment allows for precise placement of balloons and prevents a balloon from sliding out of the desired position during inflation. The manipulator 9 in FIG. 10A is shown with embedded balloons specifically tailored for cardiac surgery. In such use, the heart would be positioned with the apex resting on two balloons 80 and 81 and the base toward the first end 73 with the great vessels passing through the concave area 72. In cardiac surgery, the most common heart manipulation to position for surgical access is to roll the heart medially to gain access to the left coronary artery. Such a maneuver is accomplished by inflating a balloon 83 to accomplish a medial roll. Two other balloons 80 and 81 are inflated to lift the apex. A fourth balloon 82 stabilizes the heart during a medial roll. FIG. 10B shows another view of the manipulator 9 of FIG. 10A with the balloons 80, 81, 82 and 83 in varying degrees of inflation. The edges of the relatively rigid platform can be soft and rounded, as depicted in FIG. 10C.

FIG. 11 depicts another embodiment, where the relatively rigid platform 11 has coupled to it flexible elongated members 90, 91, 92 and 93 which can be manipulated to position the manipulator under an organ. FIG. 11A shows a lateral view of FIG. 11. FIG. 11B, FIG. 11C, FIG. 11D and FIG. 11E show how various corners of the relatively rigid platform 11 can be lifted by pulling on given flexible elongated members 90, 91, 92 and 93. FIG. 11D and FIG. 11E also show how the manipulator could be operated to allow access to the dorsal side of the heart by pulling the flexible elongated members in a cross-diagonal direction. FIG. 11F shows how the flexible elongated members may be used to position the manipulator 9 under an organ, in this case the heart 30. FIG. 11G how a given flexible elongated member 91 can be pulled ventrally and medially to roll the lateral margin of the heart medially to access portions of the anterior descending branch of the left coronary artery and the circumflex artery.

Figure 12A:
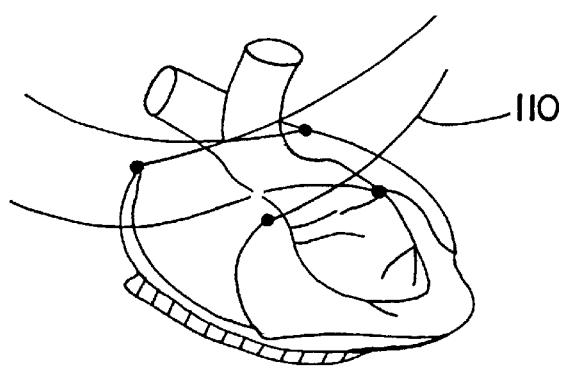
FIG. 12A shows the embodiment of FIG. 12 where the flexible cords have been used to pull the manipulator around the heart to stabilize it.
Figure 12B:
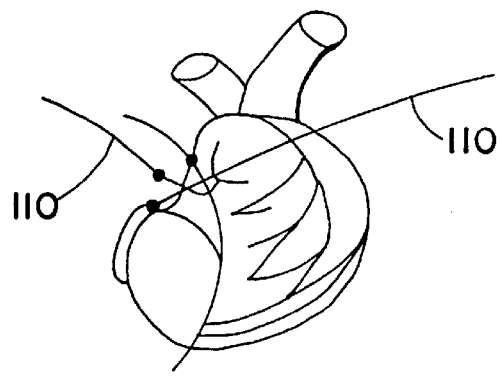
FIG. 12B shows the embodiment of FIG. 12 where the flexible cords have been manipulated to roll the lateral margin of the heart medially to access portions of the anterior descending branch of the left coronary artery and the circumflex artery.
Figure 12:
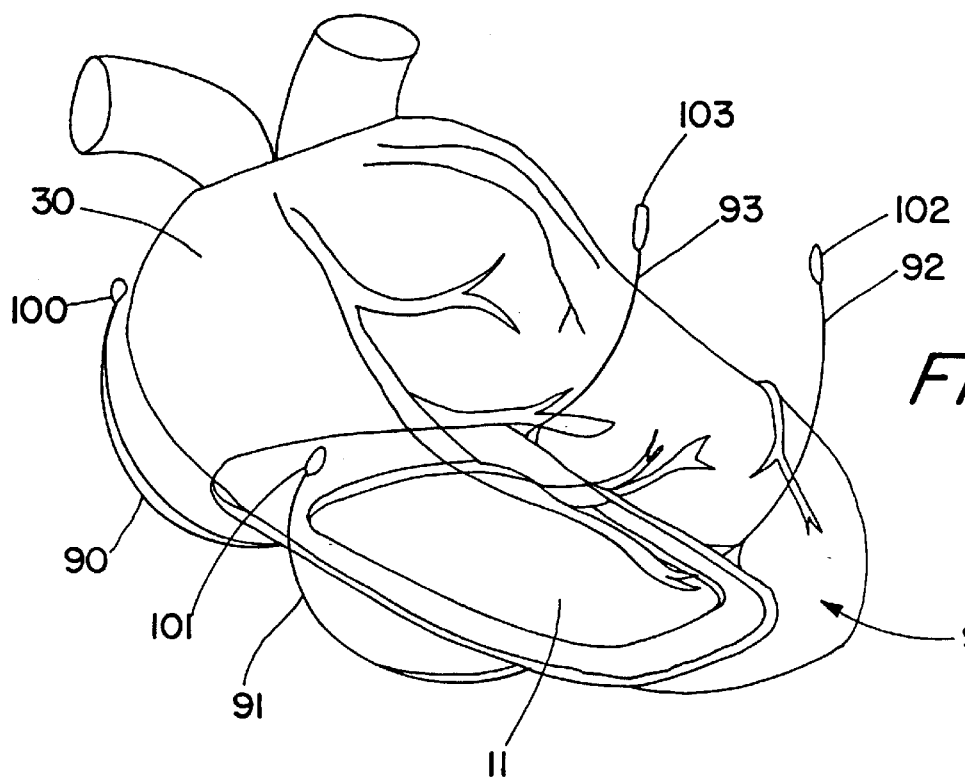
FIG. 12 shows the embodiment of FIG. 11 where the flexible elongated members have holes near one end for insertion of flexible cord.

FIG. 12 depicts another embodiment where each flexible elongated member has a hole 100, 101, 102 and 103 near one end to allow attachment of flexible cord 110 as shown in FIG. 12A and FIG. 12B. In one embodiment, the hole is a suture ring and the flexible cord is suture material. FIG. 12A and FIG. 12B show how each flexible cord can be pulled in a cross-diagonal direction to stabilize the heart and roll it medially or laterally.

Figure 13:
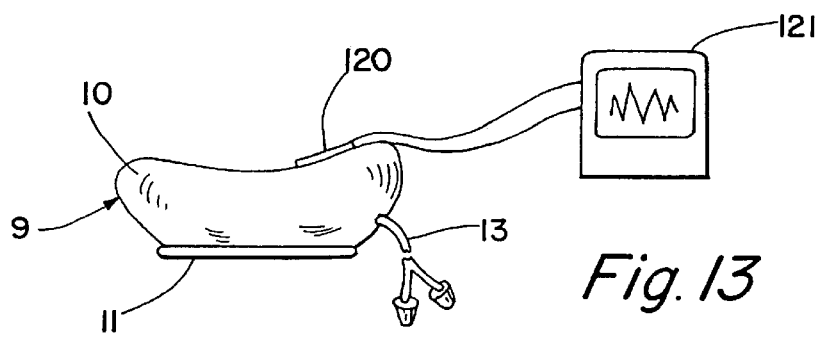
FIG. 13 shows an embodiment of a manipulator fitted with a sensor coupled to a computer.
Figure 13A:
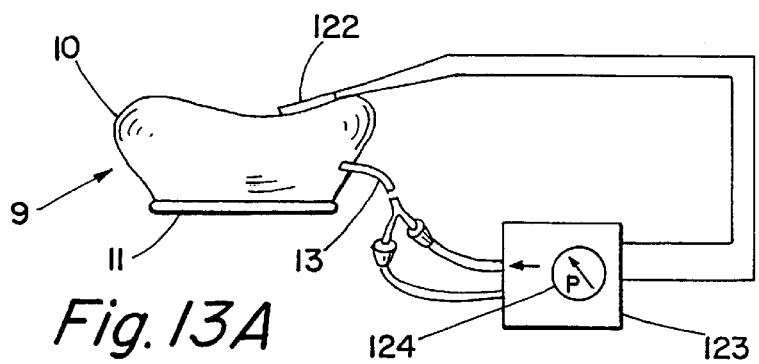
FIG. 13A shows an embodiment of a manipulator fitted with a sensor coupled to a closed-loop feedback system which has signaled a control device at the infusion source to inflate the balloon.
Figure 13B:
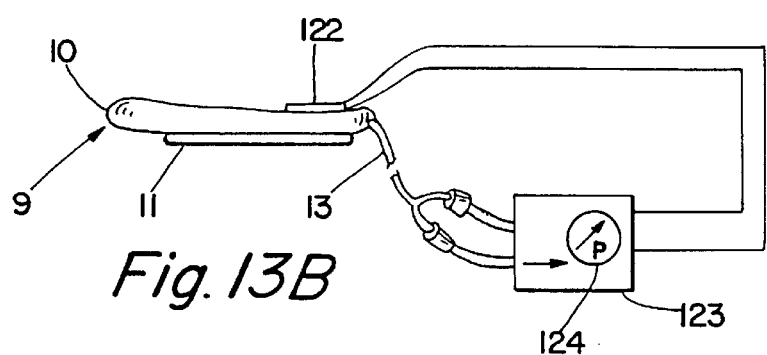
FIG. 13B shows the embodiment of FIG. 13A where the closed-loop feedback system has signaled the control device to deflate the balloon.
Figures 13C, 13D, 13E:
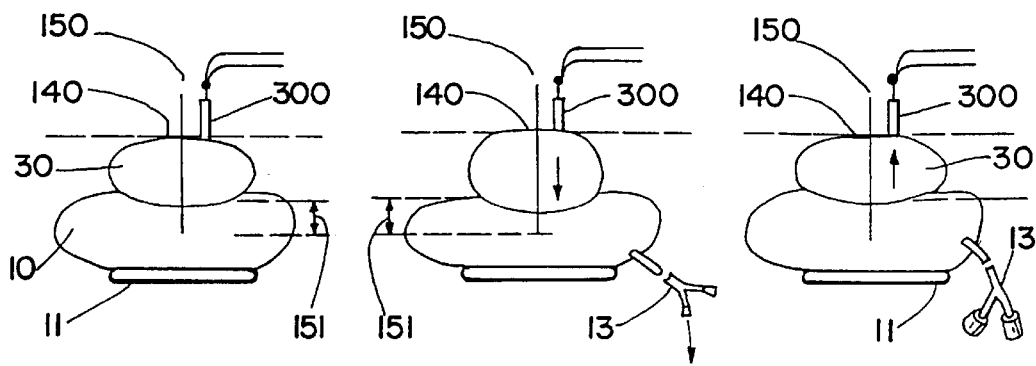
FIG. 13C shows a linear variable differential transformer ("LVDT") positioned on the heart where such LVDT would be connected to a feed-back system to adjust inflation of the balloon.
FIG. 13D shows the embodiment of FIG. 13C where the heart has expanded, and the balloon has deflated to accommodate the heart movement.
FIG. 13E shows the embodiment of FIG. 13C where the heart has contracted, and the balloon has inflated to accommodate the heart movement.

FIG. 13 depicts an embodiment where the manipulator 9 includes a sensor 120 attached to the balloon 10, where the sensor is used to detect various properties of the environment of the organ during surgery including temperature, pressure of the organ against the balloon and position of the organ. In one embodiment, the sensor is connected to a computer 121, as shown in FIG. 13. The computer can be used to monitor the properties of the environment of the organ, such as temperature and pressure, and can collect and analyze data on such properties. In another embodiment, as shown in FIG. 13A and FIG. 13B, a sensor 122 measures pressure and is connected to a closed-loop feedback control system 123 which itself is coupled to a control device at the infusion source 13. In one embodiment, the control device is a pressure regulator 124. In another embodiment shown in FIG. 13C, the sensor is a linear variable differential transformer ("LVDT") 300 attached to the heart to provide information on heart movement to a closed-loop feed-back control system which signals a control device, which can be a pressure regulator, to increase or decrease pressure in the balloon to create an offsetting motion. LVDT's can be aligned along various axes of the heart to detect heart movement in various locations. FIG. 13C, FIG. 13D and FIG. 13E show the effect of this embodiment FIG. 13C shows the heart 30 in its initial position as it rests upon the balloon 10 which is inflated. The surface 140 is the area upon which the surgical procedure is performed. In FIG. 13C, the heart begins to expand along an axis 150 thereby changing the length of the LVDT 300. The LVDT emits an electrical signal with variable output in proportion to the length of its extension. The control device receives the signal and itself signals the pressure regulator to deflate the balloon in the direction opposite the movement of the heart along the axis 150, as shown in FIG. 13D. Therefore, if the heart expands a distance 151 along the axis 150, the LVDT provides this information to the control device so that it can send a signal to the pressure regulator to deflate the balloon the same distance where the bottom surface of the heart intersects the axis 150 so that there is no net movement at 140 where the top surface of the heart intersects the axis 150. Since this top surface 140 is the area undergoing surgery, the benefit is that, although the heart may continue to move, such movement is offset and therefore absorbed by the varying pressure, and therefore volume, in the underlying balloon, creating a fixed top surface for surgery. FIG. 13E shows the completed cycle where the heart has contracted along the axis 150 and the LVDT signaled the control device to inflate the balloon to again offset the movement of the balloon in the direction opposite the movement of the heart.

Figure 14:
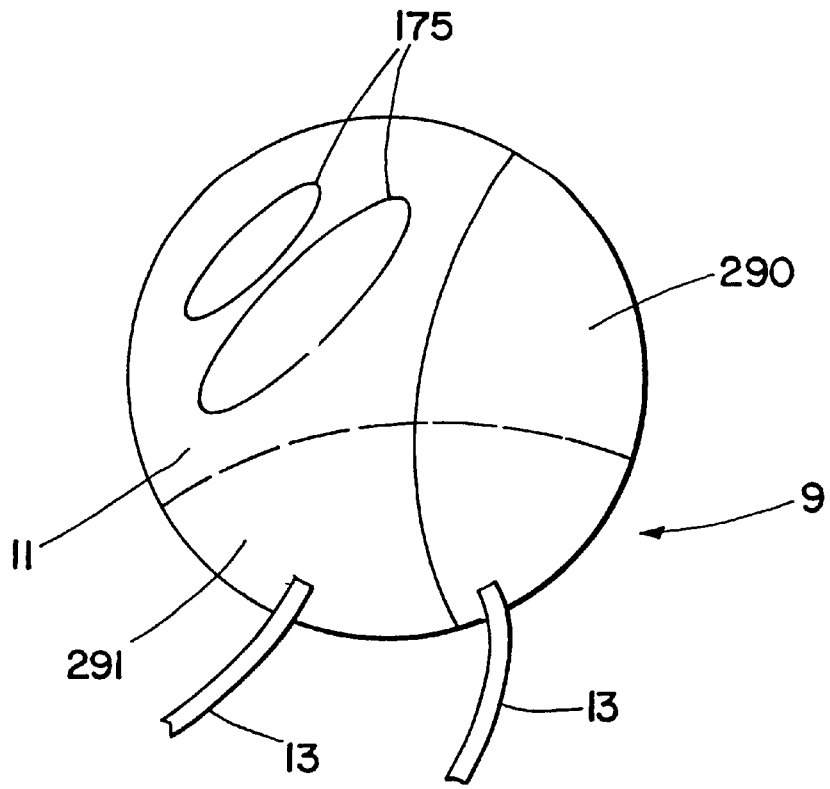
FIG. 14 depicts a top elevation of another embodiment where two single-chambered balloons have been coupled to opposite sides of a relatively rigid platform and an exposed portion of the relatively rigid platform has been roughened by forming parallel ridges its surface.

In another embodiment, the outer surface of the balloon can be roughened to enhance traction on the organ it contacts to prevent slippage of the organ. If the manipulator includes a relatively rigid platform, the platform can also be roughened to enhance traction on the adjacent surface that the platform contacts. FIG. 14 depicts an embodiment where such roughening has been accomplished by parallel ridges 175. If the manipulator includes a sheet as a positioning structure, the sheet can also be roughened. Such roughening on the balloon, the relatively rigid platform or the sheet can also be accomplished by blistering or dimpling the surface or by attaching one-half hook-and-eye or Velcro® pair.

Figure 14A:
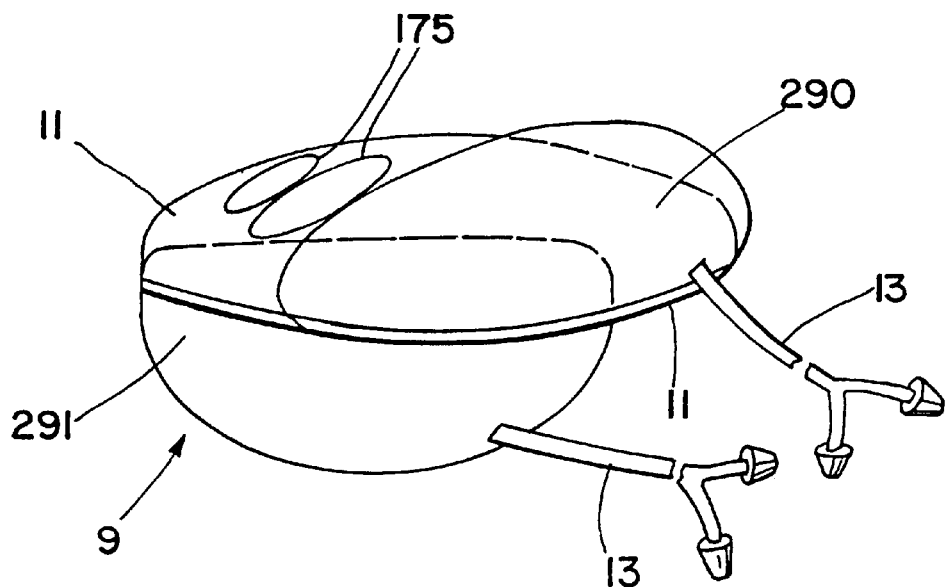
FIG. 14A shows a perspective view of the embodiment of FIG. 14.

FIG. 14 depicts an embodiment where a manipulator is formed from a relatively rigid platform 11, in this case located between two balloons 290 and 291. The area of the relatively rigid platform 11 Is also greater than the area of each of the two balloons. The top balloon 290 is displaced right laterally on the relatively rigid platform 11 and coupled to it, and the bottom balloon 291 is displaced proximally on the relatively rigid platform and coupled to it so that the two chambers are at an angle and form an inverted L-shape when viewed from a top elevation as shown in FIG. 14. The two balloons overlap when viewed from a top elevation near the right lateral proximal end of the relatively rigid platform. The exposed portion of the top surface of the relatively rigid platform in the left lateral distal end is roughened by parallel ridges 175 in its surface. This balloon configuration allows elevation of the apex and lateral margins of the heart by inflating both balloons. FIG. 14A is a perspective view of the embodiment of FIG. 14.

Figure 15:
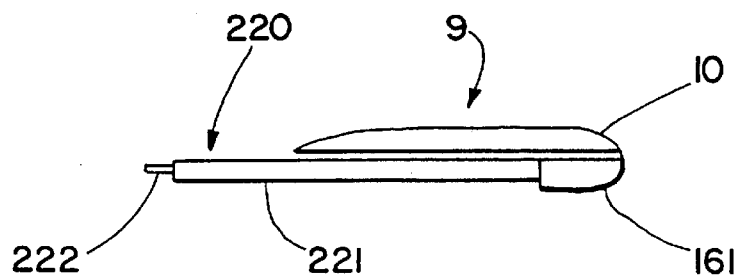
FIG. 15 shows an insertion device inside the pocket of a manipulator.
Figure 15A:
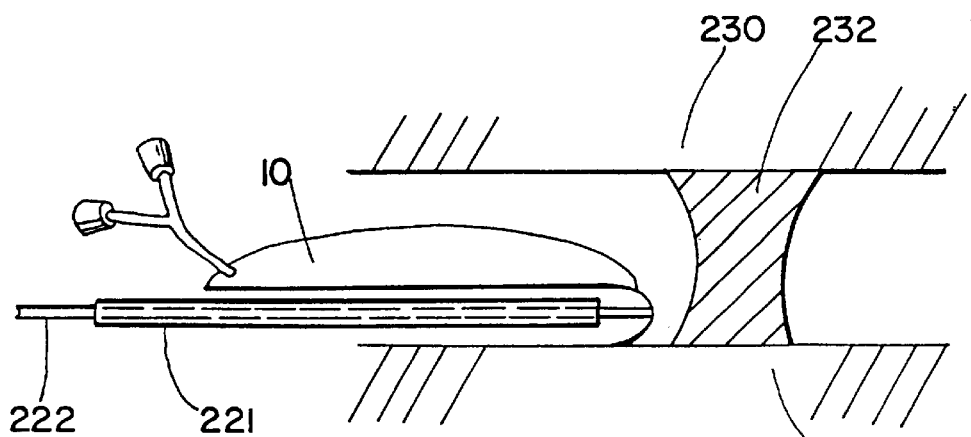
FIG. 15A shows the embodiment of FIG. 15 in a deflated condition, where the manipulator has been positioned proximal to an adhesion by an insertion device.
Figure 15B:
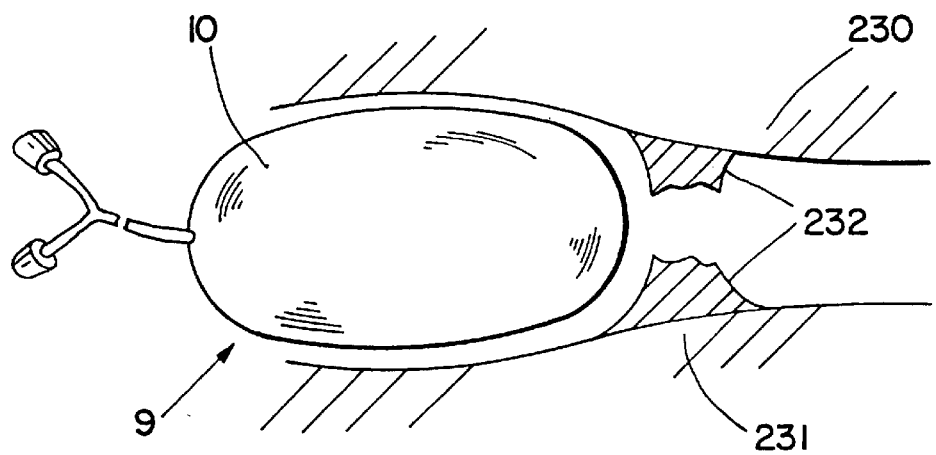
FIG. 15B shows the manipulator of FIG. 15 in an inflated condition separating the adhered layers.

FIG. 15, FIG. 15A and FIG. 15B show another method of use of the insertion device and the manipulator fitted to receive it. FIG. 15 shows the insertion device fitted into the pocket 161 of the manipulator 9. FIG. 15A shows the insertion device and manipulator inserted between two adjacent tissue layers 230 and 231 connected by an adhesion 232 where the insertion device has been used to advance the manipulator to a position just proximal to the adhesion. In FIG. 15B, the insertion device has been removed, leaving the manipulator 9 in place, the balloon 10 of the manipulator has been inflated, applying force to the adjacent adhered tissues 230 and 231 and separating the adhesion 232 by pulling apart the adjacent adhered tissues. In another method where the adhered tissue layers may not lend themselves to clean separation, the balloon can be inflated to expose the adhesion and allow access for sharp dissection. This method may be used for dissection or separation of nonvascular structures. It may be used to separate adhesions between the heart and the inner layer of the pericardium or adhesions between the two layers of the pericardium.

While particular devices and methods have been described for using inflatable manipulators to position organs during surgery, once this description is known, it will be apparent to those of ordinary skill in the art that other embodiments and alternative steps are also possible without departing from the spirit and scope of the invention. Moreover, it will be apparent that certain features of each embodiment as well as features disclosed in each reference incorporated herein, can be used in combination with devices illustrated in other embodiments. Accordingly, the above description should be construed as illustrative, and not in a limiting sense, the scope of the invention being defined by the following claims.

We claim:

1. A manipulator for displacing an organ from an adjacent anatomic structure and thereafter orienting, manipulating, retracting or stabilizing the organ during a surgical procedure, the manipulator comprising:

an inflatable balloon having a plurality of chambers, wherein the balloon is formed from a flexible sheet partially coupled to itself to form the plurality of chambers, the balloon having an inner surface and an outer surface;

an infusion source in fluid communication with the chambers of the balloon; and a flexible positioning sheet having a plurality of edges, wherein a first edge is coupled to the outer surface of the balloon and a second edge is free of the outer surface of the balloon, the positioning sheet forming a pocket having an opening at the first edge adapted to receive an insertion device.

2. The manipulator of claim 1, wherein the positioning sheet is welded along the first edge to the balloon.

3. The manipulator of claim 1, wherein the balloon is formed from a plurality of flexible sheets, the plurality of sheets forming the plurality of chambers.

4. The manipulator of claim 1, wherein the plurality of chambers are configured to be separately inflatable, the manipulator further comprising a plurality of infusion sources each in fluid communication with a separate chamber.

5. The manipulator of claim 1, wherein the balloon after inflation assumes a generally rectangular shape.

6. The manipulator of claim 1, wherein the separate chambers are formed by fusing a top and a bottom inner surface of the balloon together.

7. The manipulator of claim 1, wherein the balloon encloses a chamber having a balloon height limiter therein, the height limiter having a first end coupled to the inner surface of the first side of the balloon and a second end coupled to the inner surface of the second side of the balloon, the height limiter limiting expansion of the balloon in a region surrounding the height limiter upon inflation.

8. A manipulator for displacing an organ from an adjacent anatomic structure and thereafter orienting, manipulating, retracting or stabilizing the organ during a surgical procedure, the manipulator comprising:

an inflatable balloon formed from a flexible sheet partially coupled to itself to form a chamber, the balloon having an inner surface and an outer surface a height limiter positioned within the chamber of the balloon, the height limiter limiting expansion of the balloon in a region surrounding the height limiter upon inflation;

an infusion source in fluid communication with the chamber of the balloon; and a flexible positioning sheet having a plurality of edges, wherein a first edge is coupled to the outer surface of the balloon and a second edge is free of the outer surface of the balloon, the positioning sheet forming a pocket having an opening at the first edge adapted to receive an insertion device.

9. The manipulator of claim 8, wherein the height limiter is displaced laterally from the center of the chamber.

10. A manipulator for displacing an organ from an adjacent anatomic structure and thereafter orienting, manipulating, retracting or stabilizing the organ during a surgical procedure, the manipulator comprising:

an inflatable balloon, wherein the balloon is formed from a first flexible sheet enclosing a chamber, the balloon having an inner surface and an outer surface;

an infusion source in fluid communication with the chamber of the balloon; and a positioning sheet having a plurality of edges, wherein a first edge is coupled to the outer surface of the balloon and a second edge is free of the outer surface of the balloon, the positioning sheet forming a flap having a hole, wherein the flap is adapted to urge the manipulator into position.

11. The manipulator of claim 10, wherein the sheet is partially detachably coupled to the balloon.

* * * * *